US012262868B2

United States Patent
Stricko, III et al.

(10) Patent No.: US 12,262,868 B2
(45) Date of Patent: Apr. 1, 2025

(54) SYSTEMS AND METHODS FOR PERFORMANCE OF DEPTH SENSOR AND AUXILIARY SENSOR-BASED OPERATIONS ASSOCIATED WITH A COMPUTER-ASSISTED SURGICAL SYSTEM

(71) Applicant: Intuitive Surgical Operations, Inc., Sunnyvale, CA (US)

(72) Inventors: Robert G. Stricko, III, San Francisco, CA (US); Jacob L. Divone, Mountain View, CA (US); Glenn C. Stante, San Francisco, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 531 days.

(21) Appl. No.: 17/628,168

(22) PCT Filed: Aug. 14, 2020

(86) PCT No.: PCT/US2020/046415
§ 371 (c)(1),
(2) Date: Jan. 18, 2022

(87) PCT Pub. No.: WO2021/034682
PCT Pub. Date: Feb. 25, 2021

(65) Prior Publication Data
US 2022/0265351 A1    Aug. 25, 2022

Related U.S. Application Data

(60) Provisional application No. 62/888,115, filed on Aug. 16, 2019.

(51) Int. Cl.
*A61B 34/20* (2016.01)
*A61B 1/00* (2006.01)
(Continued)

(52) U.S. Cl.
CPC .... *A61B 1/00097* (2022.02); *A61B 1/000094* (2022.02); *A61B 1/00194* (2022.02);
(Continued)

(58) Field of Classification Search
CPC ........................... A61B 2090/064–066; A61B 2034/2055–2057; A61B 34/30–77; A61B 2034/301–744
See application file for complete search history.

(56) References Cited

U.S. PATENT DOCUMENTS

| | | |
|---|---|---|
| 2014/0018819 A1 | 1/2014 | Raj et al. |
| 2017/0181808 A1 | 6/2017 | Panescu et al. |
| 2019/0231220 A1 | 8/2019 | Refai et al. |

OTHER PUBLICATIONS

International Preliminary Report on Patentability for Application No. PCT/US2020/046415, mailed Mar. 3, 2022, 13 pages.
(Continued)

*Primary Examiner* — Colin T. Sakamoto

(57) ABSTRACT

An exemplary operation management system is configured to obtain, from a depth sensor included in an imaging device, depth data representative of a depth map for an internal space of a patient, obtain auxiliary sensor data from an auxiliary sensor not included in the imaging device, and perform, based on the depth data and the auxiliary sensor data, an operation associated with a computer-assisted surgical system configured to perform a procedure within the internal space of the patient.

20 Claims, 18 Drawing Sheets

(51) Int. Cl.
| | |
|---|---|
| *A61B 5/00* | (2006.01) |
| *A61B 5/06* | (2006.01) |
| *A61B 34/00* | (2016.01) |
| *A61B 34/30* | (2016.01) |
| *A61B 90/00* | (2016.01) |
| *G06T 7/521* | (2017.01) |
| *G06T 7/55* | (2017.01) |
| *G16H 20/40* | (2018.01) |
| *G16H 30/40* | (2018.01) |
| *G16H 40/63* | (2018.01) |

(52) U.S. Cl.
CPC .............. *A61B 34/00* (2016.02); *A61B 34/30* (2016.02); *A61B 90/361* (2016.02); *G06T 7/521* (2017.01); *G06T 7/55* (2017.01); *G16H 20/40* (2018.01); *G16H 30/40* (2018.01); *G16H 40/63* (2018.01); *A61B 2034/2055* (2016.02); *A61B 2090/061* (2016.02); *A61B 2090/064* (2016.02); *A61B 2090/371* (2016.02); *A61B 2090/373* (2016.02); *G06T 2207/30004* (2013.01)

(56) References Cited

OTHER PUBLICATIONS

Extended European Search Report for Application No. EP24195448.6, mailed on Nov. 7, 2024, 10 pages.
International Search Report and Written Opinion for Application No. PCT/US2020/046415, mailed Jan. 15, 2021, 18 pages.
Invitation to pay additional fee received from the International Search Authority for PCT/US2020/046415, mailed Nov. 12, 2020, 12 pages.
Maier-Hein L., et al., "Optical Techniques for 3D Surface Reconstruction in Computer-Assisted Laparoscopic Surgery," Medical Image Analysis, May 3, 2013, vol. 17 (8), pp. 974-996.
Penne J., et al., "Time-of-Flight 3-D Endoscopy," Big Data Analytics in the Social and Ubiquitous Context: 5th International Workshop On Modeling Social Media, MSM 2014, 5th International Workshop On Mining Ubiquitous and Social Environments, MUSE 2014 And First International Workshop On Machine, Sep. 20, 2009, vol. 12 (1), pp. 467-474.
Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

SYSTEMS AND METHODS FOR PERFORMANCE OF DEPTH SENSOR AND AUXILIARY SENSOR-BASED OPERATIONS ASSOCIATED WITH A COMPUTER-ASSISTED SURGICAL SYSTEM

RELATED APPLICATIONS

The present application is a U.S. National Stage Application under 35 U.S.C. § 371 of International Application No. PCT/US2020/046415, filed on Aug. 14, 2020, which claims priority to U.S. Provisional Patent Application No. 62/888,115, filed on Aug. 16, 2019, the contents of which are hereby incorporated by reference in their entirety.

BACKGROUND INFORMATION

During a procedure performed by a computer-assisted surgical system within an internal space of a patient, it may be desirable for a surgeon or other user to direct the computer-assisted surgical system to perform various operations in response to user input. For example, it may be desirable for the computer-assisted surgical system to measure a precise distance between user-selected points within an image captured by an imaging device that is controlled by the computer-assisted surgical system. It may also be desirable for the computer-assisted surgical system to automatically perform various operations without user input. For example, it may be desirable for the computer-assisted surgical system to automatically perform efficiency-related operations, such as preventing surgical instruments from inadvertently coming in contact with and damaging tissue within the patient. Accuracy, precision, and timely responsiveness are desirable when these and other operations are performed by a computer-assisted surgical system.

SUMMARY

The following description presents a simplified summary of one or more aspects of the systems and methods described herein. This summary is not an extensive overview of all contemplated aspects and is intended to neither identify key or critical elements of all aspects nor delineate the scope of any or all aspects. Its sole purpose is to present one or more aspects of the systems and methods described herein as a prelude to the detailed description that is presented below.

An exemplary system includes a memory storing instructions and a processor communicatively coupled to the memory and configured to execute the instructions to obtain, from a depth sensor included in an imaging device, depth data representative of a depth map for an internal space of a patient, obtain auxiliary sensor data from an auxiliary sensor not included in the imaging device, and perform, based on the depth data and the auxiliary sensor data, an operation associated with a computer-assisted surgical system configured to perform a procedure within the internal space of the patient.

An exemplary method includes obtaining, by an operation management system from a depth sensor included in an imaging device, depth data representative of a depth map for an internal space of a patient, obtaining, by the operation management system, auxiliary sensor data from an auxiliary sensor not included in the imaging device, and performing, by the operation management system based on the depth data and the auxiliary sensor data, an operation associated with a computer-assisted surgical system configured to perform a procedure within the internal space of the patient.

An exemplary non-transitory computer-readable medium stores instructions that, when executed, direct a processor of a computing device to obtain, from a depth sensor included in an imaging device, depth data representative of a depth map for an internal space of a patient, obtain auxiliary sensor data from an auxiliary sensor not included in the imaging device, and perform, based on the depth data and the auxiliary sensor data, an operation associated with a computer-assisted surgical system configured to perform a procedure within the internal space of the patient.

BRIEF DESCRIPTION OF THE DRAWINGS

The accompanying drawings illustrate various embodiments and are a part of the specification. The illustrated embodiments are merely examples and do not limit the scope of the disclosure. Throughout the drawings, identical or similar reference numbers designate identical or similar elements.

DETAILED DESCRIPTION

Systems and methods for performance of depth sensor and auxiliary sensor-based operations associated with a computer-assisted surgical system are described herein. For example, an exemplary operation management system may obtain, from a depth sensor included in an imaging device, depth data representative of a depth map for an internal space of a patient, obtain auxiliary sensor data from an auxiliary sensor not included in the imaging device, and perform, based on the depth data and the auxiliary sensor data, an operation associated with a computer-assisted surgical system configured to perform a procedure within the internal space of the patient.

The systems and methods described herein advantageously use depth data and auxiliary sensor data together to perform an operation associated with a computer-assisted surgical system. This may result in the operation being more precise, accurate, and responsive than operations performed by conventional computer-assisted surgical systems that do not have concurrent access to both types of data. These and other advantages and benefits of the systems and methods described herein will be made apparent here.

Figure 1:
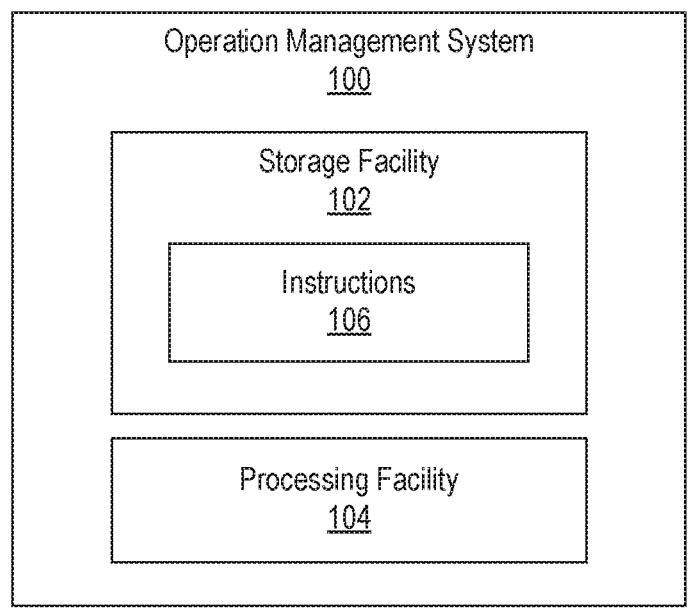
FIG. 1 illustrates an exemplary operation management system according to principles described herein.

FIG. 1 illustrates an exemplary operation management system 100 ("system 100") configured to perform depth sensor and auxiliary sensor-based operations associated with a computer-assisted surgical system. As shown, system 100 may include, without limitation, a storage facility 102 and a processing facility 104 selectively and communicatively coupled to one another. Facilities 102 and 104 may each include or be implemented by hardware and/or software components (e.g., processors, memories, communication interfaces, instructions stored in memory for execution by the processors, etc.). For example, facilities 102 and/or 104 may be implemented by any component in the computer-assisted surgical system itself. As another example, facilities 102 and/or 104 may be implemented by a computing device separate from and communicatively coupled to the computer-assisted surgical system. In some examples, facilities 102 and 104 may be distributed between multiple devices and/or multiple locations as may serve a particular implementation.

Storage facility 102 may maintain (e.g., store) executable data used by processing facility 104 to perform one or more of the operations described herein. For example, storage facility 102 may store instructions 106 that may be executed by processing facility 104 to perform one or more of the operations described herein. Instructions 106 may be implemented by any suitable application, software, code, and/or other executable data instance. Storage facility 102 may also maintain any data received, generated, managed, used, and/or transmitted by processing facility 104.

Processing facility 104 may be configured to perform (e.g., execute instructions 106 stored in storage facility 102 to perform) various operations described herein. For example, processing facility 104 may be configured to obtain, from a depth sensor included in an imaging device, depth data representative of a depth map for an internal space of a patient. Processing facility 104 may be further configured to obtain auxiliary sensor data from an auxiliary sensor not included in (or otherwise a part of) the imaging device. Processing facility 104 may be further configured to perform, based on the depth data and the auxiliary sensor data, an operation associated with a computer-assisted surgical system configured to perform a procedure within the internal space of the patient. These and other operations that may be performed by system 100 (e.g., processing facility 104) are described herein.

Figure 2:
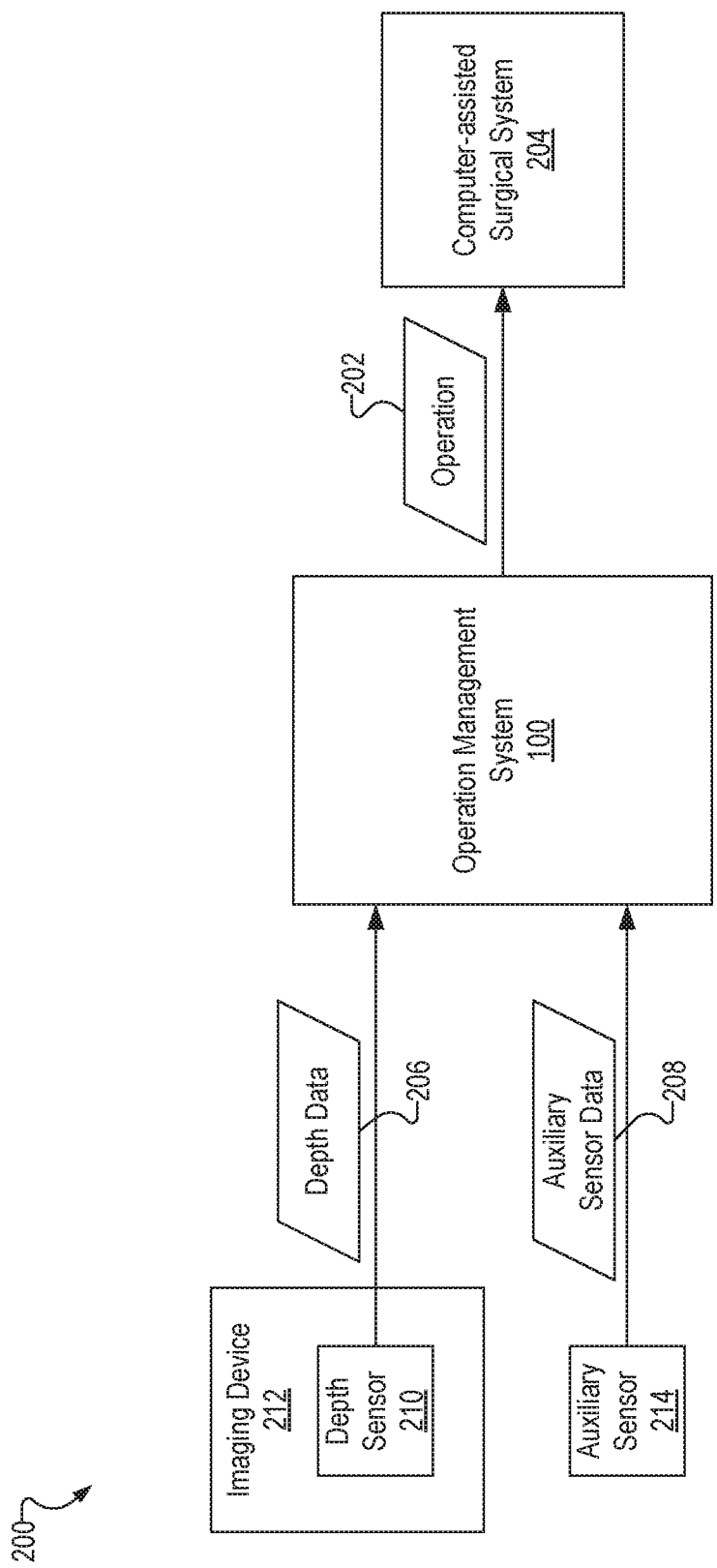
FIG. 2 illustrates an exemplary configuration in which the operation management system of FIG. 1 performs an operation associated with a computer-assisted surgical system based on depth data and auxiliary sensor data according to principles described herein.

FIG. 2 illustrates an exemplary configuration in which system 100 performs an operation 202 associated with a computer-assisted surgical system 204 based on depth data 206 and auxiliary sensor data 208. As shown, system 100 obtains depth data 206 from a depth sensor 210 included in an imaging device 212. System 100 obtains auxiliary sensor data 208 from an auxiliary sensor 214 not included in imaging device 212.

Computer-assisted surgical system 204 may be implemented by any suitable surgical system that uses robotic and/or teleoperation technology to perform a procedure (e.g., a minimally invasive surgical procedure) within an internal space of (e.g., a surgical area within) a patient. An exemplary computer-assisted surgical system is described herein.

Operation 202 may include any suitable operation performed with respect to computer-assisted surgical system 204. In cases where system 100 is implemented by computer-assisted surgical system 204 itself, operation 202 may be performed by computer-assisted surgical system 204. Examples of operation 202 are described herein.

Imaging device 212 may be implemented by an endoscope or other camera device configured to capture images of a scene. In some examples, imaging device 212 may be configured to be attached to and controlled by computer-assisted surgical system 204. In alternative examples, imaging device 212 may be hand-held and operated manually by an operator (e.g., a surgeon).

In some examples, the scene captured by imaging device 212 may include a surgical area associated with a patient. The surgical area may, in certain examples, be entirely disposed within the patient and may include an area within the patient at or near where a surgical procedure is planned to be performed, is being performed, or has been performed. For example, for a minimally invasive surgical procedure being performed on tissue internal to a patient, the surgical area may include the tissue, anatomy underlying the tissue, as well as space around the tissue where, for example, surgical instruments used to perform the surgical procedure are located. In certain example implementations, the surgical area entirely disposed within the patient may be referred to as an "internal space". As described herein, any internal anatomy of the patient (e.g., vessels, organs, and/or tissue) and/or surgical instruments located in the internal space may be referred to as objects and/or structures.

Depth sensor 210 included in imaging device 212 may be implemented by any suitable sensor configured to generate depth data 206 representative of a depth map for an internal space of a patient. For example, as described herein, depth sensor 210 may be implemented by a time-of-flight sensor, a structured light sensor, an interferometer, stereoscopic cameras, and/or any other suitable components as may serve a particular implementation.

Auxiliary sensor 214 may be implemented by any suitable sensor not included in or otherwise a part of imaging device 212. For example, as described herein, auxiliary sensor 214 may be implemented by a user input sensor configured to generate user input data, a force sensor integrated into a surgical instrument controlled by computer-assisted surgical system 204 and configured to output force sensing data representative of an amount of external force applied to the surgical instrument, and/or any other type of sensor configured to output any other type of auxiliary sensor data 208 as may serve a particular implementation.

Various exemplary manners in which system 100 may obtain depth data 206 from depth sensor 210 in imaging device 212 will now be described.

Figure 3:
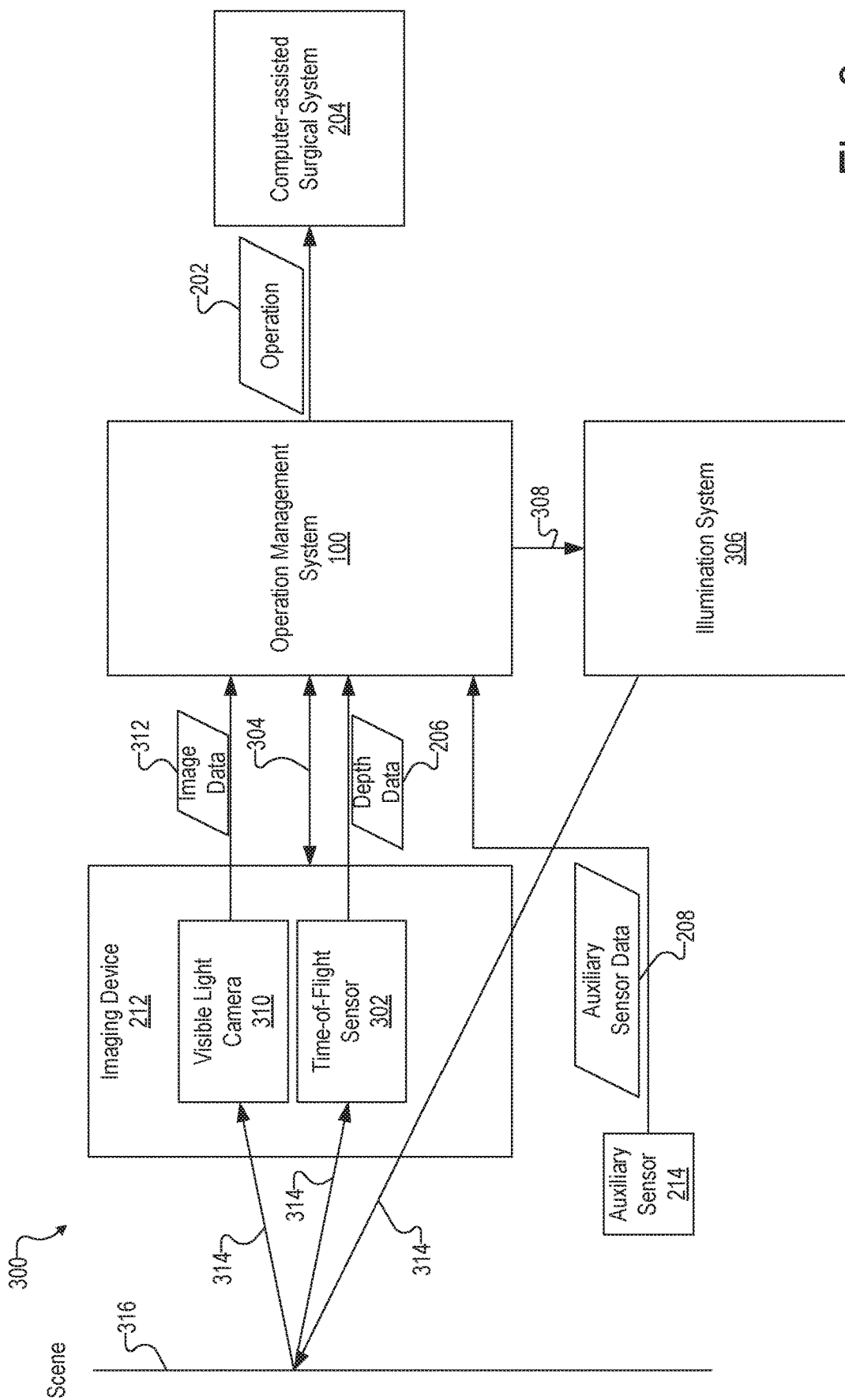
FIG. 3 illustrates an exemplary implementation in which a depth sensor is implemented by a time-of-flight sensor included in an imaging device according to principles described herein.

FIG. 3 illustrates an exemplary implementation 300 in which depth sensor 210 is implemented by a time-of-flight sensor 302 included in imaging device 212, While time-of-flight sensor 302 is shown in FIG. 3 and referred to in the examples provided herein, any other type of depth sensor separate from (i.e., physically distinct from) a visible light camera also included in imaging device 212 may additionally or alternatively be used to implement depth sensor 210. For example, depth sensor 210 may alternatively be implemented by a structured light sensor, an interferometer, and/or any other suitable sensor configured to acquire depth data as may serve a particular implementation.

In implementation 300, system 100 may obtain depth data 206 by directing time-of-flight sensor 302 to acquire depth data 206 and receiving depth data 206 from time-of-flight sensor 302.

To this end, in implementation 300, system 100 is communicatively coupled to imaging device 212 by way of a bidirectional communication link 304 and to an illumination system 306 by way of a communication link 308. Communication links 304 and 308 may each be implemented by any suitable wired and/or wireless communication medium as may serve a particular implementation. System 100 may use communication links 304 and 308 to direct time-of-flight sensor 302 to acquire depth data 206 and receive depth data 206 from time-of-flight sensor 302, as will be described herein.

As shown, imaging device 212 includes time-of-flight sensor 302 and a visible light camera 310 ("camera 310"), which is configured to generate image data 312 representative of a two-dimensional visible light image of a scene. Time-of-flight sensor 302 may be implemented by one or more photodetectors (e.g., one or more single photon avalanche diode ("SPAD") detectors), CCD sensors, CMOS sensors, and/or any other suitable configuration configured to obtain depth data of a scene. Camera 310 may be implemented by any suitable image sensor, such as a charge coupled device ("CCD") image sensor, a complementary metal-oxide semiconductor ("CMOS") image sensor, or the like.

In some examples, system 100 may be configured to control an operation of imaging device 212 (e.g., by controlling an operation of camera 310 and time-of-flight sensor 302). For example, system 100 may include one or more camera control units ("CCUs") configured to control various parameters (e.g., activation times, auto exposure, etc.) of camera 310 and/or time-of-flight sensor 302.

System 100 may additionally or alternatively be configured to provide operating power for components included in imaging device 212. For example, while imaging device 212 is communicatively coupled to system 100, system 100 may transmit operating power to camera 310 and time-of-flight sensor 302 in the form of one or more power signals.

System 100 may be configured to use imaging device 212 and illumination system 306 to acquire depth data 206 and image data 312. In some examples, depth data 206 and image data 312 may be used to generate stereoscopic images of a scene. This will be described in more detail below.

Illumination system 306 may be configured to emit light 314 (e.g., at the direction of system 100) used to illuminate a scene to be imaged by imaging device 212. The light 314 emitted by illumination system 306 may include visible light and/or non-visible light (e.g., infrared light). As shown, light 314 may travel to the scene through imaging device 212 (e.g., by way of an illumination channel within imaging device 212 that may be implemented by one or more optical fibers, light guides, lenses, etc.). Various implementations and configurations of illumination system 306 are described herein.

As shown, light 314 emitted by illumination system 306 may reflect off a surface 316 within a scene being imaged by imaging device 212. Visible light camera 310 and time-of-flight sensor 302 may each detect the reflected light 314. Visible light camera 310 may be configured to generate, based on the detected light, image data 312 representative of a two-dimensional visible light image of the scene including surface 316. Time-of-flight sensor 302 may be configured to generate, based on the detected light, depth data 206. Image data 312 and depth data 206 may each have any suitable format.

To generate a stereoscopic image of a scene, system 100 may direct illumination system 306 to emit light 314. System 100 may also activate (e.g., turn on) visible light camera 310 and time-of-flight sensor 302. Light 314 travels to the scene and reflects off of surface 316 (and, in some examples, one or more other surfaces in the scene). Camera 310 and time-of-flight sensor 302 both detect the reflected light 314.

Camera 310 (and/or other circuitry included in imaging device 212) may generate, based on detected light 314, image data 312 representative of a two-dimensional visible light image of the scene. This may be performed in any suitable manner. Visible light camera 310 (and/or other circuitry included imaging device 212) may transmit image data 312 to system 100, This may also be performed in any suitable manner.

Time-of-flight sensor 302 may generate, based on detected light 314, depth data 206 representative of a depth map of the scene (e.g., a depth map of surface 316). This may be performed in any suitable manner. For example, time-of-flight sensor 302 may measure an amount of time that it takes for a photon of light 314 to travel from illumination system 306 to time-of-flight sensor 302. Based on this amount of time, time-of-flight sensor 302 may determine a depth of surface 316 relative to a position of time-of-flight sensor 302. Data representative of this depth may be represented in depth data 206 in any suitable manner. For example, the depth map represented by depth data 206 may include an array of depth values (e.g., Z-buffer values) corresponding to each pixel in an image.

Time-of-flight sensor 302 (and/or other circuitry included imaging device 212) may transmit depth data 206 to system 100. This may be performed in any suitable manner.

System 100 may receive image data 312 and depth data 206 and perform one or more processing operations on image data 312 and depth data 206, For example, based on image data 312 and depth data 206, system 100 may generate a right-side perspective image of the scene and a left-side perspective image representative of the scene. This may be performed in any suitable manner. System 100 may then direct display devices to concurrently display the right and left-side perspective images in a manner that forms a stereoscopic image of the scene. In some examples, the display devices are included in and/or communicatively coupled to computer-assisted surgical system 204.

System 100 may perform operation 202 based on depth data 206. In some examples, operation 202 may be additionally based on image data 312, Examples of operation 202 are described herein.

Figure 4:
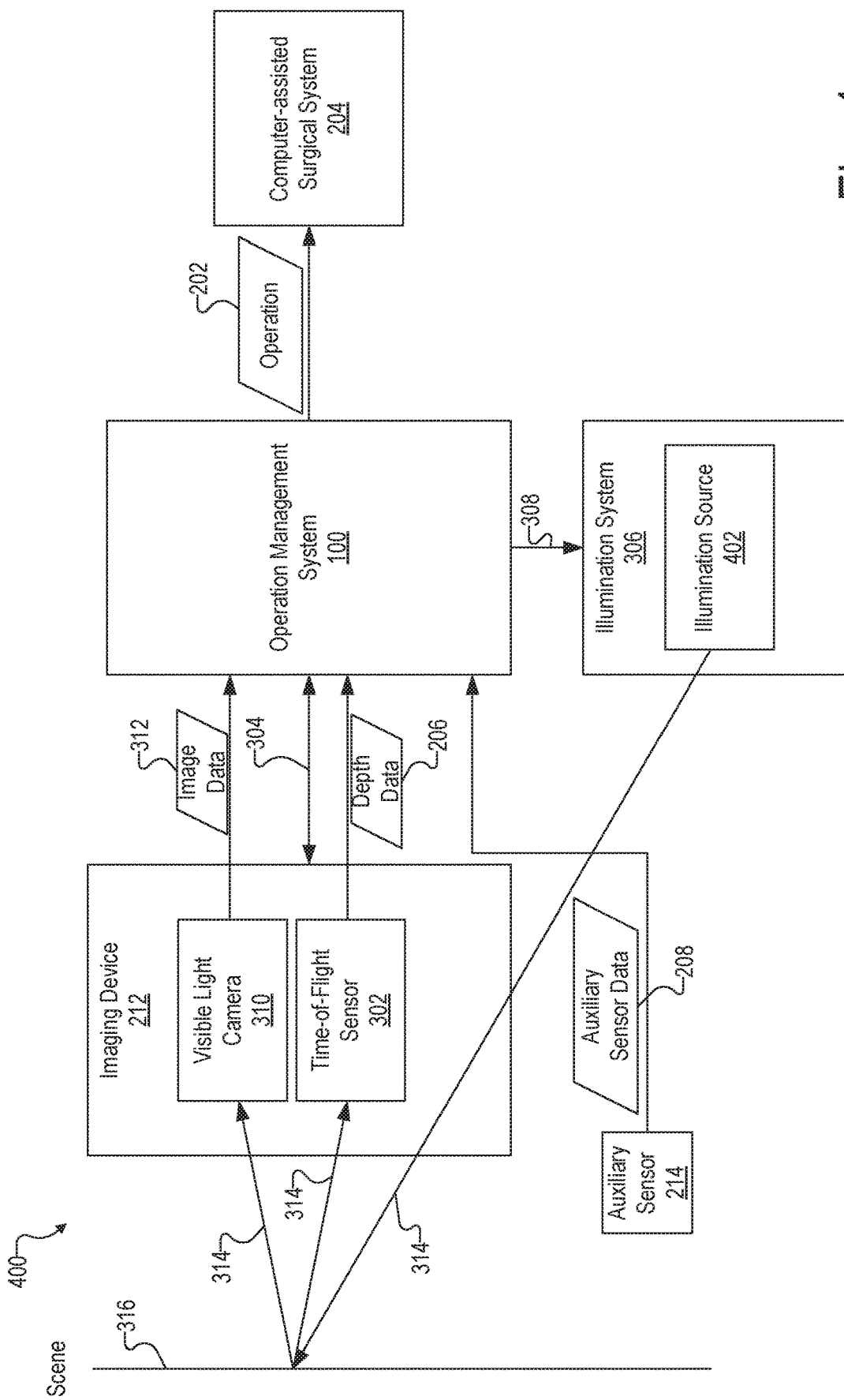
FIG. 4 shows an exemplary implementation in which an illumination system is implemented by a single illumination source according to principles described herein.

FIG. 4 shows an exemplary implementation 400 in which illumination system 306 is implemented by a single illumination source 402. Illumination source 402 may be configured to emit visible light 314-1.

Visible light 314-1 may include one or more color components. For example, visible light 314-1 may include white light that includes a full spectrum of color components (e.g., red, green, and blue color components). The red color component has wavelengths between approximately 935 and 700 nanometers ("nm"). The green color component has wavelengths between approximately 720 and 760 nm. The blue color component has wavelengths between approximately 650 and 690 nm.

In some examples, visible light 314-1 is biased to include more of one color component than another color component. For example, visible light 314-1 may be blue-biased by including more of the blue color component than the red and green color components.

In implementation 400, time-of-flight sensor 302 is configured to also detect visible light 314-1. Accordingly, the same illumination source 402 may be used for both camera 310 and time-of-flight sensor 302.

Figure 5:
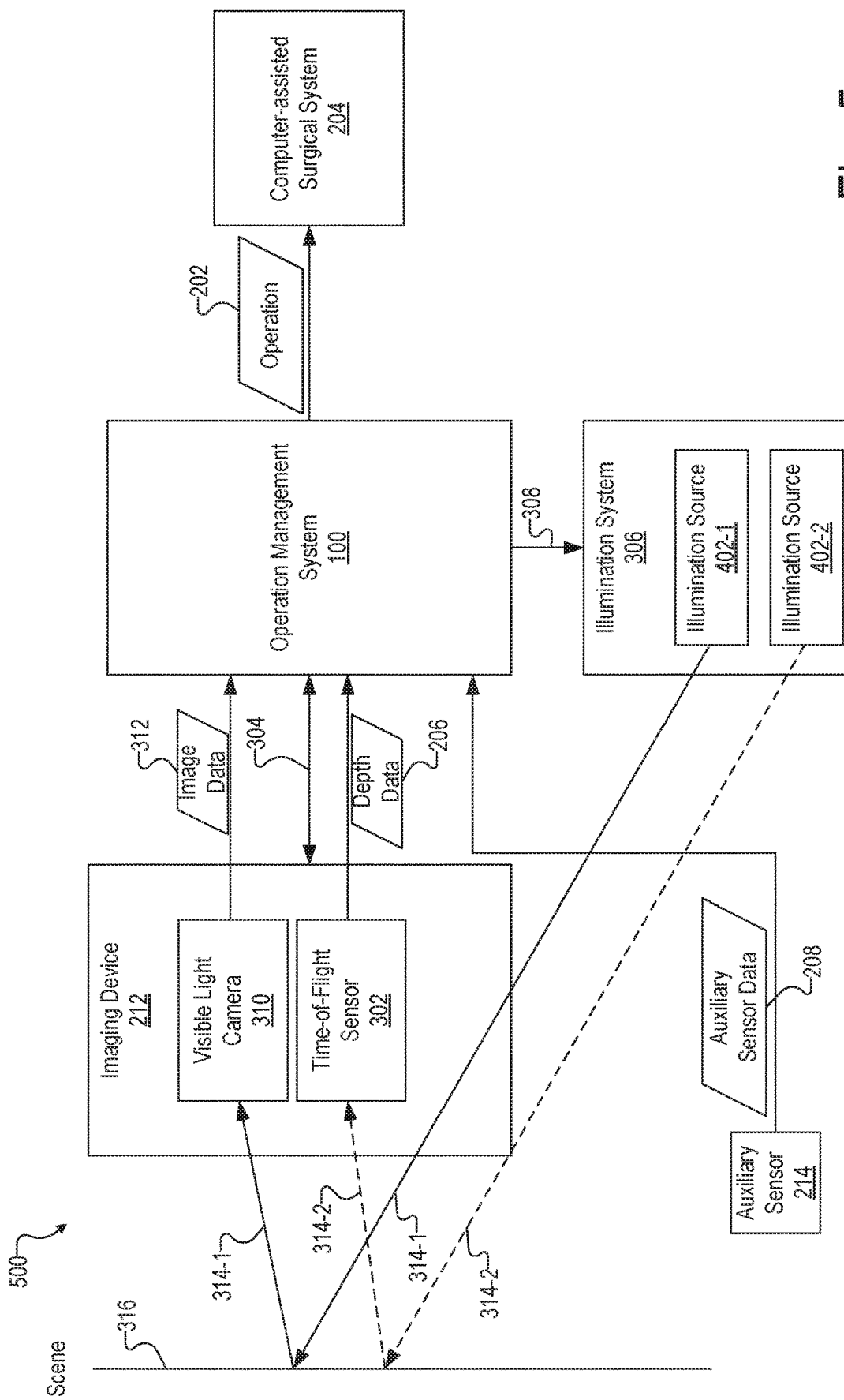
FIG. 5 illustrates an exemplary implementation in which an illumination system is implemented by separate illumination sources according to principles described herein.

FIG. 5 illustrates an exemplary implementation 500 in which illumination system 306 is implemented by separate illumination sources 402-1 and 402-2. In implementation 500, illumination source 402-1 is configured to emit visible light 314-1 that is detected by camera 310. Illumination source 402-2 is configured to emit light 314-2 that reflects from surface 316 and is detected by time-of-flight sensor 302. In some examples, light 314-2 is non-visible light, such as infrared light. By having separate illumination sources 402 for camera 310 and time-of-flight sensor 302, camera 310 and time-of-flight sensor 302 may be configured to operate independently.

Figure 6:
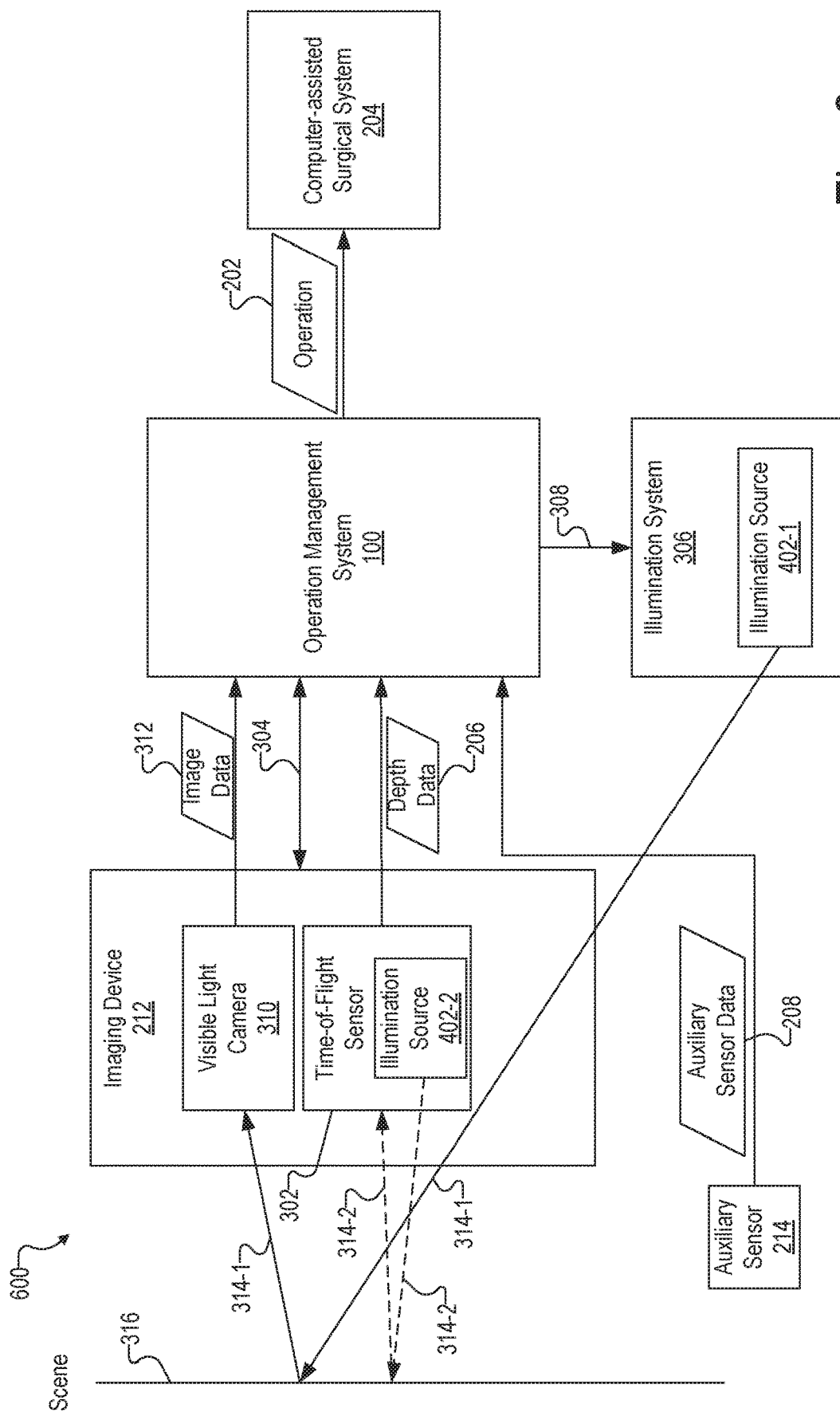
FIG. 6 illustrates an exemplary implementation in which an illumination source is integrated into a time-of-flight sensor according to principles described herein.

FIG. 6 illustrates an exemplary implementation 600 in which illumination source 402-2 is integrated into time-of-flight sensor 302. In implementation 600, system 100 may control (e.g., activate) illumination source 402-2 by transmitting instructions to time-of-flight sensor 302.

Figure 7:
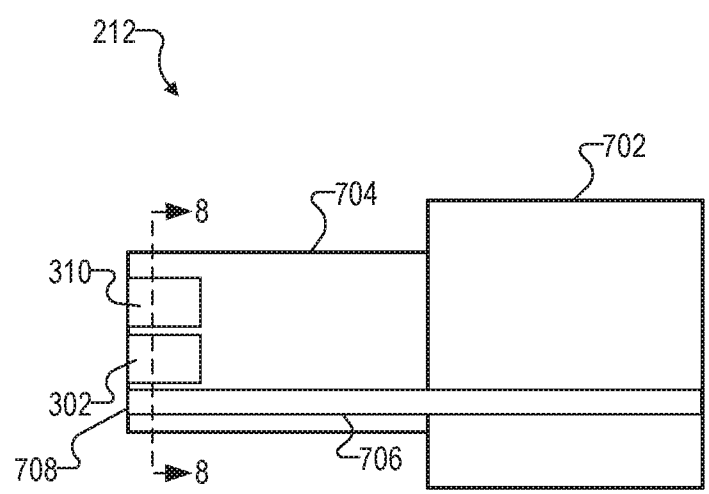
FIG. 7 illustrates an exemplary structural implementation of imaging device according to principles described herein.
Figure 8:
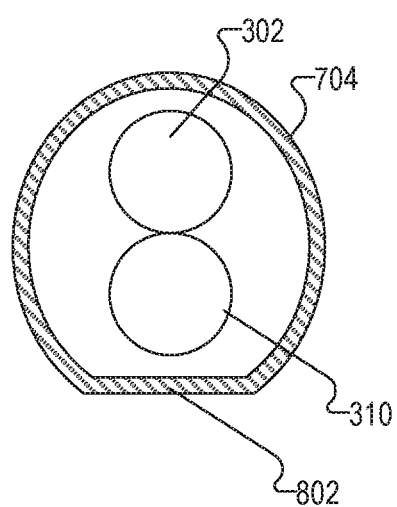
FIG. 8 depicts a cross-sectional view of a shaft of an imaging device according to principles described herein.

FIG. 7 illustrates an exemplary structural implementation of imaging device 212. As shown, imaging device 212 includes a camera head 702 and a shaft 704 coupled to and extending away from camera head 702. Camera head 702 and shaft 704 together implement a housing of imaging device 212. Imaging device 212 may be manually handled and controlled (e.g., by a surgeon performing a surgical procedure on a patient). Alternatively, camera head 702 may be coupled to a manipulator arm of computer-assisted surgical system 204. In this configuration, imaging device 212 may be controlled by computer-assisted surgical system 204 using robotic and/or teleoperation technology.

As shown, an illumination channel 706 may pass through camera head 702 and shaft 704. Illumination channel 706 is configured to provide a conduit for light emitted by illumination system 306 to travel to a scene that is being imaged by imaging device 212.

A distal end 708 of shaft 704 may be positioned at or near a scene that is to be imaged by imaging device 212, For example, distal end 708 of shaft 704 may be inserted into a patient. In this configuration, imaging device 212 may be used to capture images of anatomy and/or other objects within the patient.

Camera 310 and time-of-flight sensor 302 may be located anywhere along shaft 704 of imaging device 212, In the example shown in FIG. 7, camera 310 and time-of-flight sensor 302 are located at distal end 708 of shaft 704. This configuration may be referred to as a "chip on tip" configuration. Alternatively, camera 310 and/or time-of-flight sensor 302 may be located more towards camera head 702 and/or within camera head 702. In these alternative configurations, optics (e.g., lenses, optical fibers, etc.) included in shaft 704 and/or camera head 206 may convey light from a scene to camera 310 and/or time-of-flight sensor 302.

In some examples, camera 310 and time-of-flight sensor 302 may be staggered at different distances from distal end 708 of shaft 704. By staggering the distances of camera 310 and time-of-flight sensor 302 from distal end 708 of shaft 704, imaging device 212 may take on a tapered configuration with a reduced size (e.g., diameter) towards distal end 708 of the shaft 704, which may be helpful for inserting the imaging device 212 into an internal space of a patient.

Figure 9:
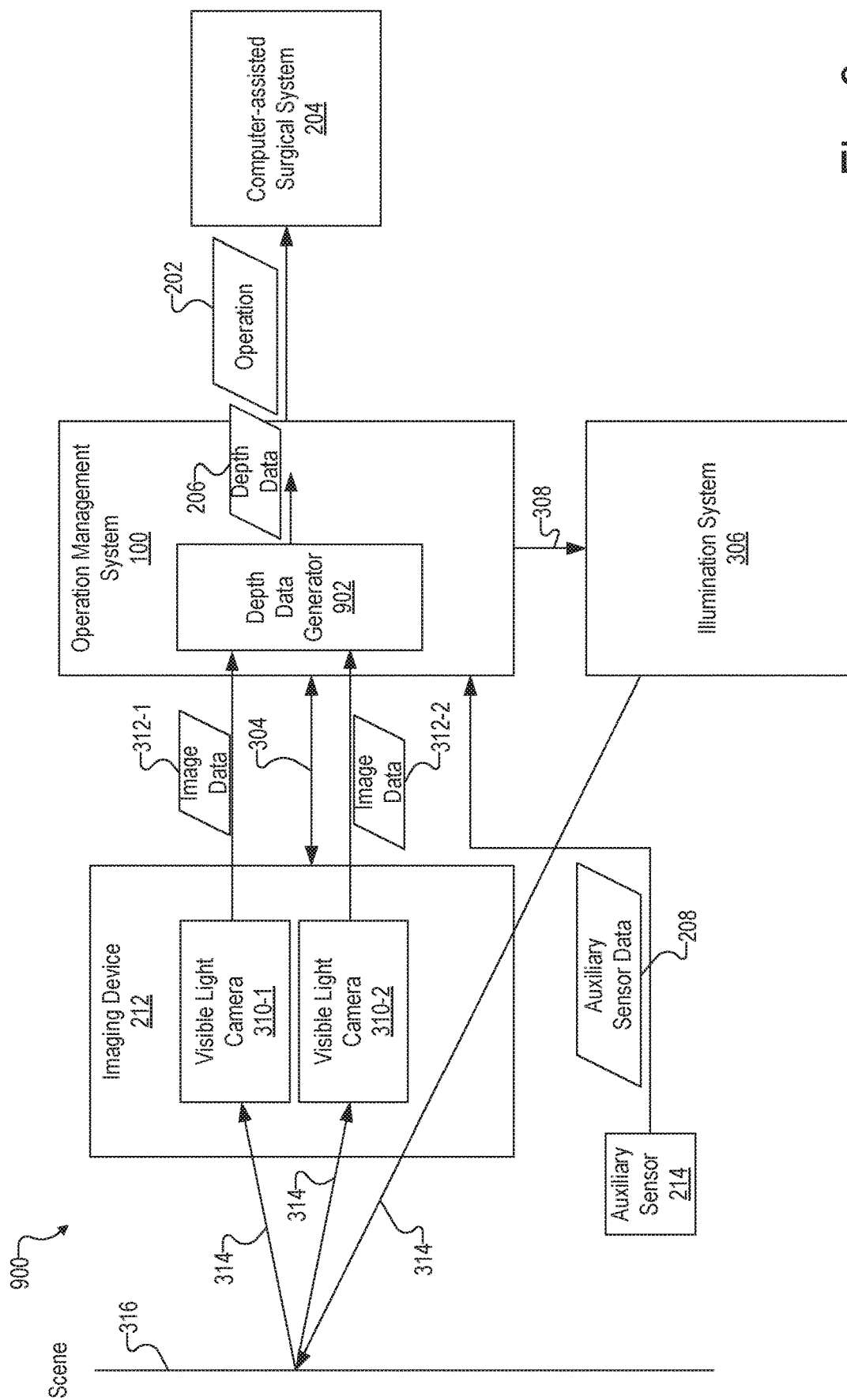
FIG. 9 illustrates an exemplary implementation in which a depth sensor is implemented by visible light cameras included in imaging device according to principles described herein.

FIG. 9 depicts a cross-sectional view of shaft 704 of imaging device 212 taken along lines 9-8 in FIG. 7. As shown, shaft 704 includes a relatively flat bottom surface 902. With reference to this bottom surface 902, time-of-flight sensor 302 is positioned above camera 310. Such positioning may allow for a more narrow shaft 704 compared to shafts of conventional imaging devices that have two cameras side-by-side in order to acquire stereoscopic images. It will be recognized that camera 310 and time-of-flight sensor 302 may have any suitable relative position within shaft 704 as may serve a particular implementation.

FIG. 9 illustrates an exemplary implementation 900 in which depth sensor 210 is implemented by visible light cameras 310-1 and 310-2 included in imaging device 212. In implementation 900, system 100 may obtain depth data 206 by directing camera 310-1 to acquire a first image (e.g., a first two-dimensional image) of an internal space of a patient, directing camera 310-2 to acquire a second image (e.g., a second two-dimensional image) of the internal space of the patient, and generating, based on the first and second images, the depth map represented by depth data 206.

In FIG. 9, the first image acquired by camera 310-1 is represented by image data 312-1 and the second image acquired by camera 310-2 is represented by image data 312-2. As shown, image data 312-1 and 312-2 are transmitted to a depth data generator 902 implemented by system 100. Depth data generator 902 may use any visible image-based technique to determine depth data 206 based on image data 312-1 and 312-2.

Various examples of operation 202 that may be performed by system 100 with respect to computer-assisted surgical system 204 based on depth data 206 will now be provided. These examples are merely illustrative of the many different types of operations that may be performed by system 300 based on depth data 206 in accordance with the systems and methods described herein.

In some examples, system 100 may perform operation 202 by determining a distance between endpoints within an image of an internal space of the patient as acquired by imaging device 212. The image may, in some examples, be a two-dimensional image acquired by visible light camera 310 and represented by image data 312. Additionally or alternatively, the image may be a stereoscopic image generated based on image data 312 and depth data 206 in any of the ways described herein.

In the examples in which system 100 performs operation 202 by determining a distance between endpoints within an image of an internal space of the patient, auxiliary sensor 214 may be implemented by a user input sensor. The user input sensor may be configured to sense user input, such as user input provided by way of a keyboard, a touch screen, etc. In these examples, system 100 may be configured to obtain auxiliary sensor data 208 by receiving, from the user input sensor, user input data indicating a selection by a user of a first two-dimensional endpoint within an image of the internal space. As described herein, the first two-dimensional endpoint corresponds to a first feature within the internal space as depicted by the image. System 100 may perform operation 202 by defining, based on depth data 206 acquired by time-of-flight sensor 302 and on the user input data, a first three-dimensional endpoint corresponding to the first feature and determining, based on depth data 206 acquired by time-of-flight sensor 302, a distance from the first three-dimensional endpoint corresponding to the first feature to a second three-dimensional endpoint corresponding to a second feature within the internal space. Because depth data 206 acquired by time-of-flight sensor 302 is relatively precise, system 100 may determine a relatively precise distance measurement in accordance with the systems and methods described herein.

Figure 10:
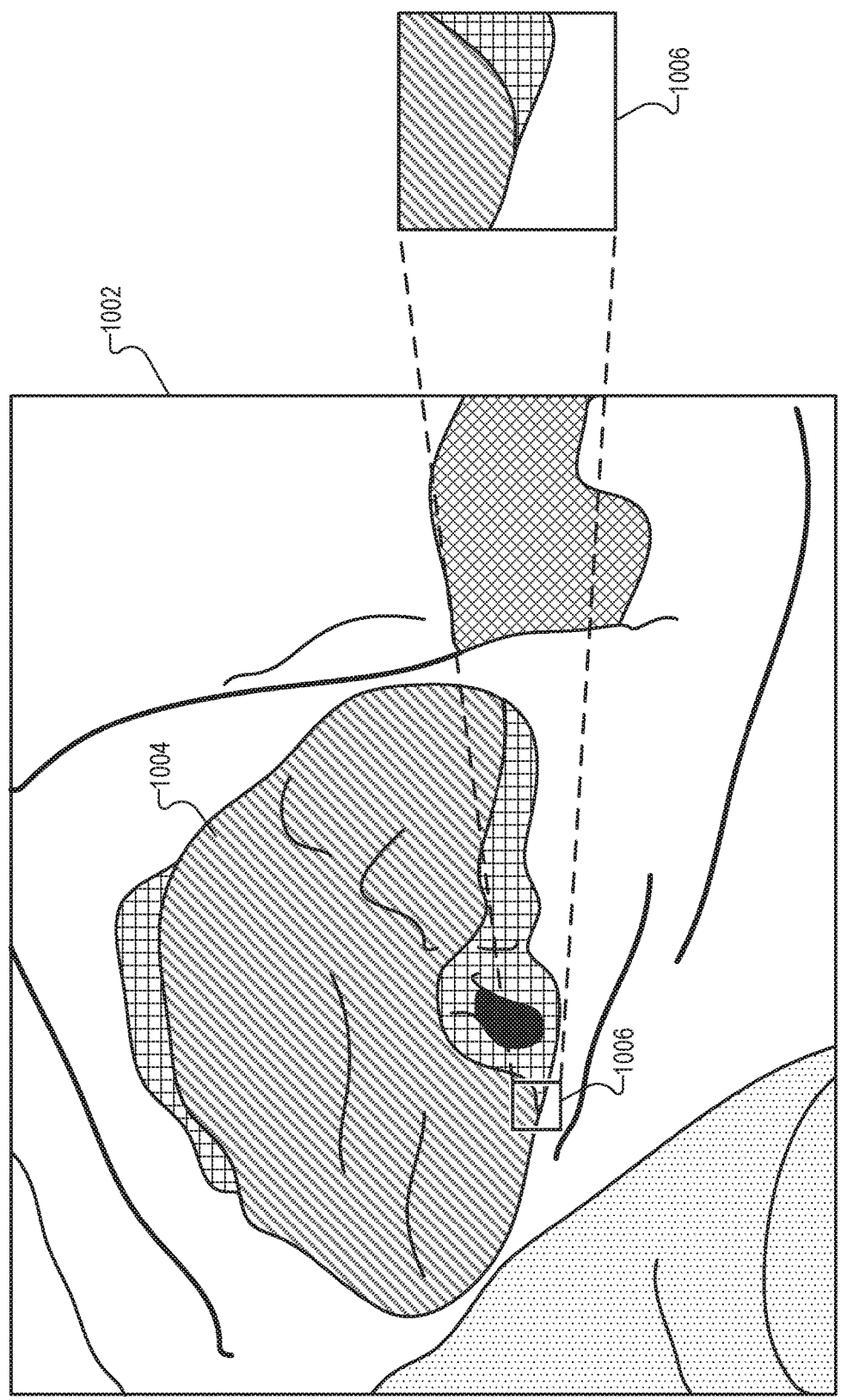
FIG. 10 illustrates an exemplary two-dimensional image according to principles described herein.

FIG. 10 illustrates an exemplary two-dimensional image 1002 of an internal space of a patient as captured by camera 310 included in imaging device 212 and represented by image data 312. As shown, image 1002 depicts a representation of a hernia 1004 that is to be measured so that, for example, a mesh patch may be cut to an appropriate size to properly patch the hernia 1004.

Image 1002 may be displayed or presented by system 600 in any suitable way and/or on any suitable display screen. For instance, image 1002 may be displayed on a display screen of a display device included in and/or communicatively coupled to computer-assisted surgical system 204.

To measure a distance between features displayed in image 1002 (e.g., a distance between edges of hernia 1004), or between a feature displayed in image 1002 and an additional feature not currently displayed in image 1002, a user may interact with image 1002 to provide user input designating one or more user-selected two-dimensional endpoints that correspond to the feature(s). Auxiliary sensor 214 may detect the user input.

To illustrate, FIG. 10 illustrates an exemplary user-selected two-dimensional endpoint 1006 designated by a user on image 1002. User-selected two-dimensional endpoint 1006 may correspond to a particular feature. As used herein, a "feature" to which an endpoint (e.g., a two-dimensional or three-dimensional endpoint) corresponds may refer to a particular component, point, or other feature of an anatomical structure or other object within an internal space of a patient. For example, the feature to which user-selected two-dimensional endpoint 1006 corresponds is a particular part of an edge of hernia 1004 (enlarged on the right-hand side of FIG. 10 to illustrate the feature in more detail). User-selected two-dimensional endpoint 1006 may include a plurality of pixels that collectively depict the corresponding feature.

Auxiliary sensor 214 (in this case implemented by a user input sensor) may detect, receive, and/or sense any suitable type of user input designating user-selected two-dimensional endpoint 1006. For example, the user may provide the user input by touching a location on the touch screen that corresponds to the desired feature (e.g., an edge of hernia 1004) displayed within image 1002. Auxiliary sensor 214 may detect the user touching the touch screen and output auxiliary sensor data 208 representative of the location.

In some examples, user-selected two-dimensional endpoint 1006 may be designated by a surgeon or other user of computer-assisted surgical system 204 using a stereo viewer. For example, right and left-perspective images generated in any of the ways described herein and that together form a stereoscopic image may be displayed on right and left image display screens, respectively, of a stereo viewer. In this example, a pointer object may be made to appear to be floating above tissue depicted in the scene until user-selected two-dimensional endpoint 1006 is selected, at which point the cursor may appear to on to the tissue at a proper depth as a corresponding three-dimensional endpoint is defined (as will be described below). Additionally, as yet another example, the user may select a point in a stereoscopic image using a three-dimensional cursor. A projection of this selected point onto a two-dimensional image (e.g., image 1002) may then be used as user-selected two-dimensional endpoint 1006.

In some examples, a designation of a user-selected two-dimensional endpoint (e.g., user-selected two-dimensional endpoint 1006) may be performed as a discrete event such as a touch gesture, a button press, a mouse click, a button release (e.g., to end a dragging motion from one user-selected two-dimensional endpoint to another), or the like. In other examples, the user selection of the user-selected two-dimensional endpoint may be performed dynamically as a pointer object (e.g., a cursor) is moved within a display screen without any additional user selection action (i.e., without an action such as a button press, mouse click, or the like). In other words, in certain implementations, many user-selected two-dimensional endpoints for many different potential measurements may be automatically selected as a user moves the pointer object on the display.

Once user-selected two-dimensional endpoint 1006 corresponding to a feature has been designated within image 1002 by a user in any of these or other suitable ways, system 100 may define, based on depth data 206 acquired by time-of-flight sensor 302 and on the user input designating two-dimensional endpoint 1006, a first three-dimensional endpoint corresponding to the feature. This may be performed in any suitable manner. For example, depth data 206 may indicate depth values for the pixels that constitute two-dimensional endpoint 1006. Accordingly, these depth values may be used to define a three-dimensional endpoint that represents a three-dimensional location of the feature.

System 100 may determine a distance between the first three-dimensional endpoint corresponding to the first feature and a second three-dimensional endpoint corresponding to a second feature in any suitable manner. The second three-dimensional endpoint may be selected or defined in the same manner as described above (e.g., the user may select a second two-dimensional endpoint representative of the second feature within image 1002 and system 100 may define, based on depth data 206, the second three-dimensional endpoint). Alternatively, the second three-dimensional endpoint may be associated with a position of a known location such as a position of a surgical instrument, a position of imaging device 212, an origin point of a coordinate system, or the like. In these examples, it thus may not be necessary for a user to designate the second user-selected two-dimensional endpoint based on a feature presented in a two-dimensional image. Instead, the user may indicate that the additional three-dimensional endpoint corresponds to the particular surgical instrument, endoscope, origin point, or other known location in any suitable way.

Figure 11:
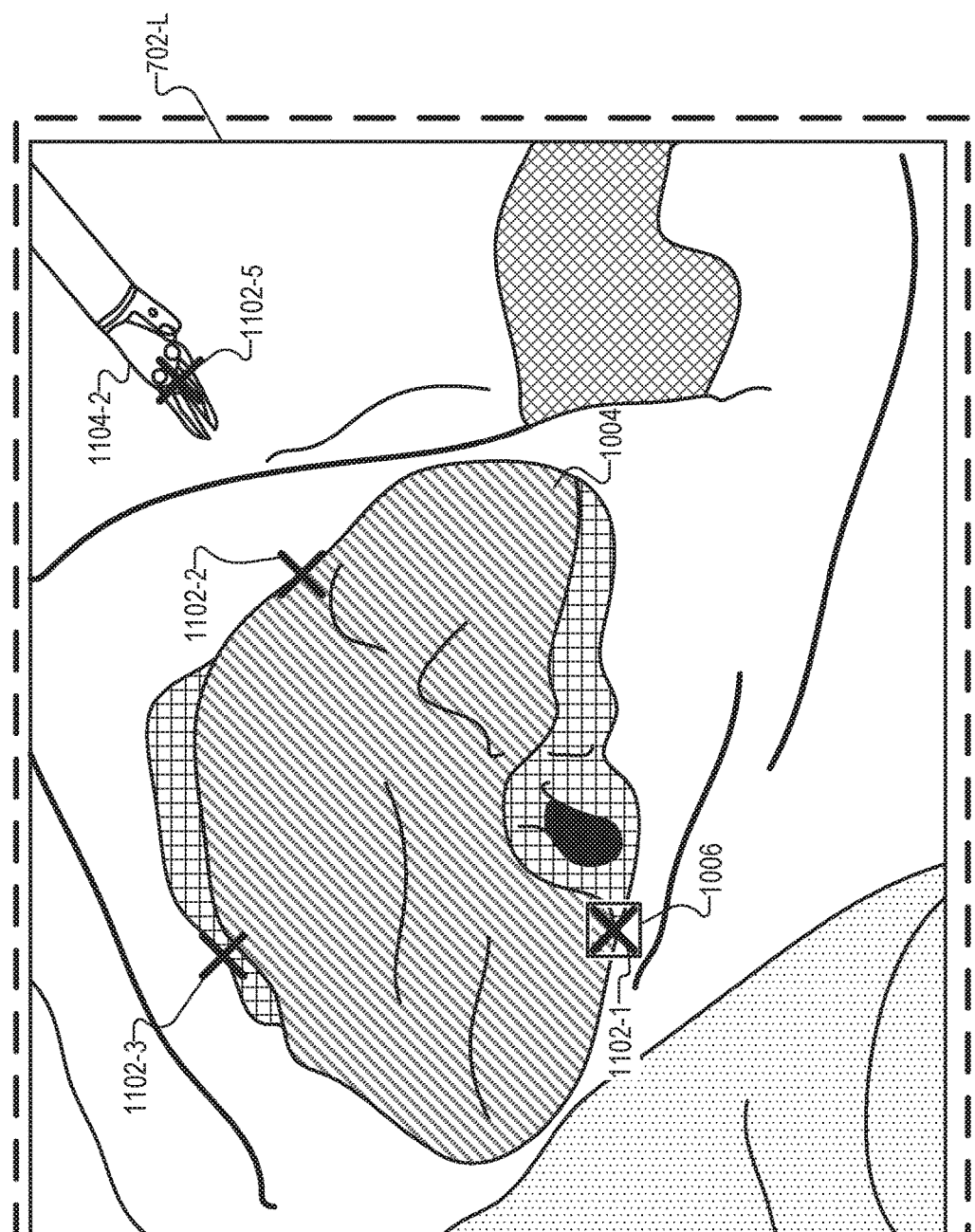
FIG. 11 illustrates exemplary three-dimensional endpoints between which one or more distances may be determined according to principles described herein.

To illustrate, FIG. 11 illustrates exemplary three-dimensional endpoints 1102 (e.g., three-dimensional endpoints 1102-1 through 1102-6) between which one or more distances may be determined. As shown in FIG. 11, a first three-dimensional endpoint 1102-1 defined based on user-selected two-dimensional endpoint 1006 within image 1002 may be positioned at a first edge of hernia 1004. Once this first three-dimensional endpoint 1102-1 is defined based on user-selected two-dimensional endpoint 1006, a distance may be determined from three-dimensional endpoint 1102-1 to any additional three-dimensional endpoint represented by three-dimensional endpoints 1102-2 through 1102-6. For instance, a distance from one edge to another of hernia 1004 may be determined by determining a distance between three-dimensional endpoint 1102-1 and one of three-dimensional endpoints 1102-2 and 1102-3.

In other examples, the additional feature to which the additional three-dimensional endpoint 1102 corresponds may be a non-anatomical feature (i.e., a feature included within the surgical area that is not part of the patient's anatomy). For instance, three-dimensional endpoint 1102-4 may be associated with a tip of a surgical instrument 1104-1, which is not currently represented within image 1002 but may still be within the internal space of the patient. As another example, three-dimensional endpoint 1102-5 may be associated with a tip of surgical instrument 1104-2, which is represented within image 1002. As yet another example, three-dimensional endpoint 1102-6 may be associated with a tip of imaging device 212 (depicted as a dotted line around image 1002). In examples where a non-anatomical feature to which a three-dimensional endpoint corresponds is not represented within image 1002 (e.g., for the features to which three-dimensional endpoints 1102-4 and 1102-6 correspond), kinematic data may be used to determine the coordinates of the three-dimensional endpoint 1102. Kinematic and/or image data 312 may be used to determine the coordinates of non-anatomical features that are represented within image 1002, such as the coordinates of three-dimensional endpoint 1102-5.

In examples where a distance to be determined is from an anatomical feature to a non-anatomical feature such as a surgical instrument 1104 hovering above the anatomical feature, it may be useful to measure a direct point-to-point distance between the two three-dimensional endpoints. However, in various other examples such as those involving three-dimensional endpoints associated with two anatomical features, it may be desirable to measure a contoured distance from one three-dimensional endpoint to the other along the contours of the tissue (i.e., rather than directly through the tissue). For instance, in the example described above in which a distance across hernia 1004 is to be measured so that a mesh patch may be cut to an appropriate size, it may be desirable to determine the distance across hernia 1004 along the surface of hernia 1004 rather determining the distance passing directly through hernia 1004.

Figure 12:
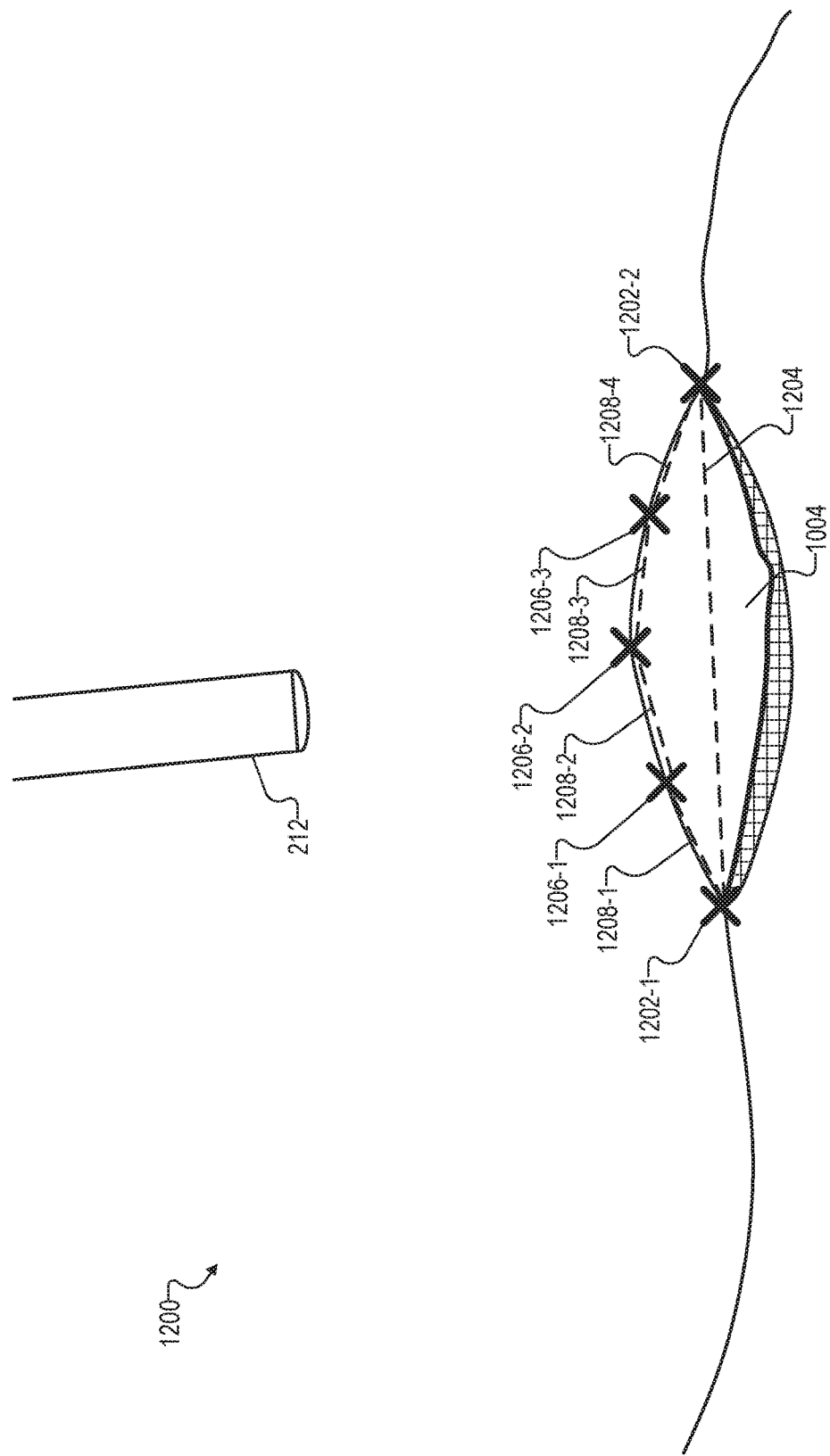
FIG. 12 shows an exemplary side view of an internal space of a patient according to principles described herein.

To illustrate, FIG. 12 shows an exemplary side view 1200 of an internal space that includes imaging device 212 imaging hernia 1004. FIG. 12 shows exemplary aspects of how a contoured distance from one three-dimensional endpoint to an additional three-dimensional endpoint may be estimated. Specifically, as shown in side view 1200, three-dimensional endpoints 1202-1 and 1202-2 (collectively referred to as "three-dimensional endpoints 1202") may be located at opposite edges of hernia 1004. In FIG. 12, a direct point-to-point distance 1204 is drawn between three-dimensional endpoints 1202, passing directly through tissue of hernia 1004. While point-to-point distance 1204 may be useful in certain contexts, it may not be an ideal distance to use for sizing a mesh patch to cover hernia 1004, since the mesh patch will need to cover the surface of hernia 1004. Accordingly, it may be desirable to determine a distance over the surface of hernia 1004, which may be referred to herein as a "contoured distance" over the tissue.

To determine this contoured distance, system 100 may, based on depth data 206 and image data 312, automatically identify one or more three-dimensional midpoints 1206 (e.g., three-dimensional midpoints 1206-1 through 1206-3 and/or additional three-dimensional midpoints not explicitly shown) on a three-dimensional contour that connects the three-dimensional endpoint to the additional three-dimensional endpoint and that runs along a physical surface upon which the three-dimensional endpoint and the additional three-dimensional endpoint are both disposed (i.e., the outer surface of hernia 1004). System 100 may then determine, based on three-dimensional midpoints 1206, intermediate distances 1208 (e.g., intermediate distances 1208-1 through 1208-4) for each segment of a linearly-segmented route from three-dimensional endpoint 1202-1 to three-dimensional endpoint 1202-2 that passes through each adjacent three-dimensional midpoint 1206 so as to substantially adhere to the three-dimensional contour between three-dimensional endpoints 1202. Based on intermediate distances 1208, system 100 may compute the contoured distance from three-dimensional endpoint 1202-1 to three-dimensional endpoint 1202-2 as a sum of intermediate distances 1208. The sum of intermediate distances 1208 may provide an estimation for an exact contoured distance that becomes more accurate as more three-dimensional midpoints 1206 and more intermediate distances 1208 are defined.

In some examples, a user may define three-dimensional midpoints 1206 manually (e.g., by selecting two-dimensional midpoints point by point) or may define a two-dimensional line along which three-dimensional midpoints 1206 are to be defined. For example, a touch screen may be used to draw a line along anatomy presented on the touch screen (e.g.; from one side to the other of hernia 1004) to designate user-selected two-dimensional endpoints as well as midpoints between them. Auxiliary sensor 214 may detect this user input. Based on the user input, system 100 may estimate a contoured distance between the endpoints by estimating a distance along the contours of tissue connecting the endpoints by way of the midpoints. In other examples, other types of user interfaces such as pointer-based interfaces may be employed to achieve a similar result.

Additionally or alternatively, system 100 may perform operation 202 by performing an efficiency-related operation associated with computer-assisted surgical system 204. For example, system 100 may perform operation 202 by controlling a movement of a surgical instrument connected to computer-assisted surgical system 204 in a manner that prevents harm from being afflicted on the patient.

To illustrate, auxiliary sensor 214 may be implemented by a force sensor integrated into a surgical instrument controlled by computer-assisted surgical system 204. The force sensor may be configured to generate force sensing data representative of an amount of external force applied to the surgical instrument. Based on the force sensing data and depth data 206, system 100 may determine that the surgical instrument begins moving towards a structure (e.g., an organ or other tissue) located in the internal space of a patient in response to external force applied to the surgical instrument. In response, system 100 may instruct computer-assisted surgical system 204 to stop the movement of the surgical instrument towards the structure before the surgical instrument damages the structure (e.g., by plunging into the structure).

Figure 13:
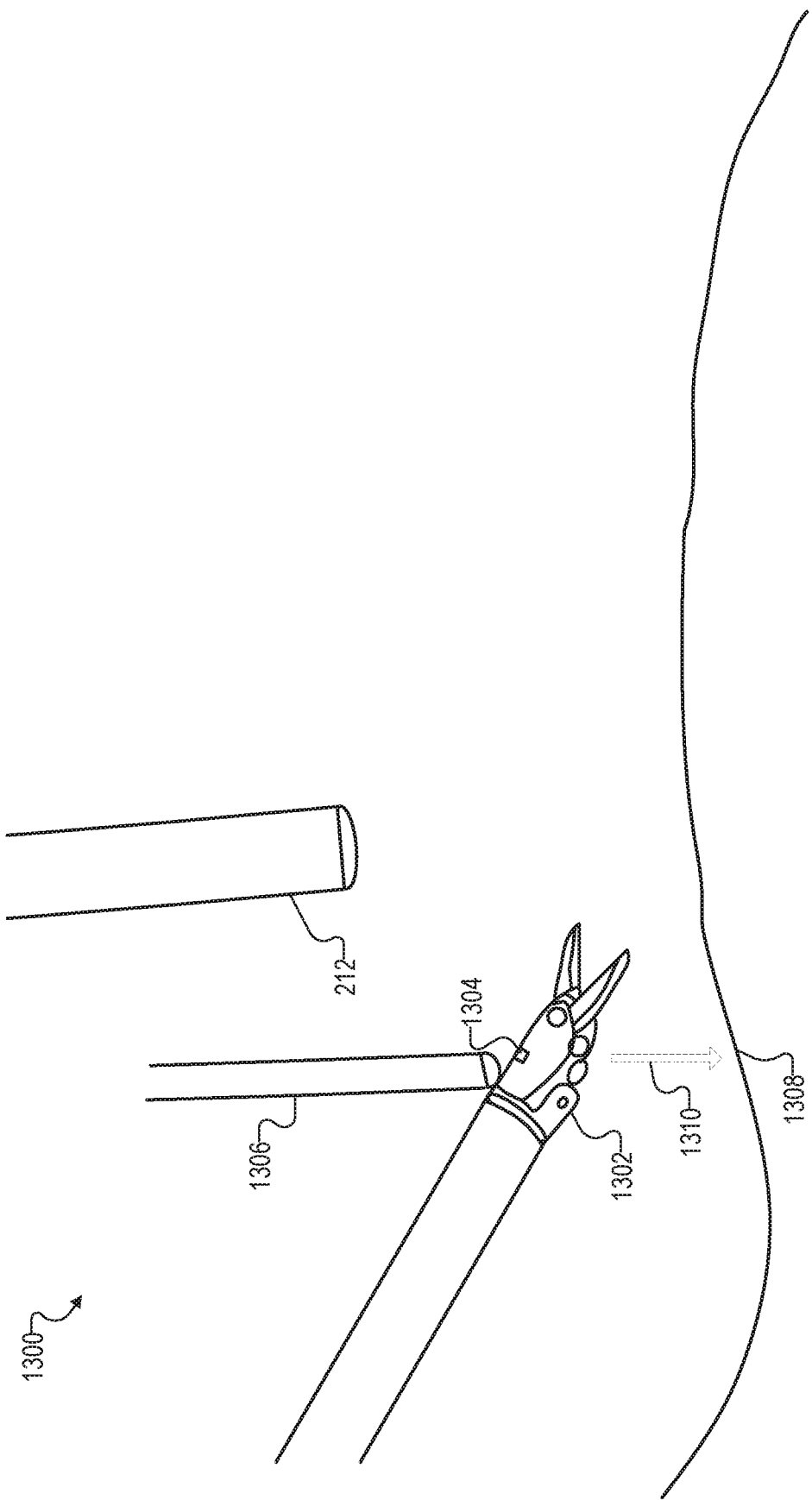
FIG. 13 shows an exemplary configuration in which a surgical instrument is being used within an internal space that is being imaged by an imaging device according to principles described herein.

To illustrate, FIG. 13 shows an exemplary configuration 1300 in which a surgical instrument 1302 is being used within an internal space that is being imaged by imaging device 212. As shown, surgical instrument 1302 includes a force sensor 1304. Force sensor 1304 may be integrated into surgical instrument 1302 in any suitable manner. For example, as shown, force sensor 1304 may be disposed on an outer surface of surgical instrument 1302. Additionally or alternatively, force sensor 1304 may be housed within surgical instrument 1302, While FIG. 13 shows force sensor 1304 located towards a distal end of surgical instrument 1302, it will be recognized that force sensor 1304 may be located at any position on or within surgical instrument 1302 as may serve a particular implementation. Moreover, in some examples, surgical instrument 1302 may include a plurality of force sensors at different locations on and/or within surgical instrument 1302.

In some examples, a user (e.g., a surgeon) may remotely control movement of surgical instrument 1302 by using his or her hands to interact with a set of master controls configured to detect a wide variety of hand, wrist, and/or finger movements by the user. In response to the user manipulating the master controls, computer-assisted surgical system 204 may move and/or otherwise manipulate surgical instrument 1302 in a corresponding manner.

However, in some cases, an unexpected force may be applied to surgical instrument 1302 that causes the user's hands to become disengaged from the master controls. In these cases, surgical instrument 1302 may inadvertently move in an uncontrolled manner and/or at an uncontrolled speed. This may cause surgical instrument 1302 to undesirably come in contact with and/or plunge into a structure (e.g., an organ or other tissue) within the patient. This contact may cause damage to the structure.

To illustrate, while a surgeon is remotely controlling movement of surgical instrument 1302, an assistant located in the operating room may be using a laparoscopic tool 1306 to perform a laparoscopic operation within the patient. While so doing, the assistant made inadvertently cause laparoscopic tool 1306 to collide with surgical instrument 1302. This collision may cause the surgeon's hands to become disengaged from the master controls being used to control surgical instrument 1302. This, in turn, may cause surgical instrument 1302 to move towards structure 1308 in a direction illustrated by arrow 1310.

Hence, in accordance with the systems and methods described herein, depth data 206 generated by depth sensor 210 within imaging device 212 in combination with force sensing data generated by force sensor 1304 may be used to determine that surgical instrument 1302 begins moving towards structure 1308 in response to external force applied by laparoscopic tool 1306. The force sensing data indicate a strength and a direction of the force. Based on this data, system 100 may determine an approximate direction and speed at which surgical instrument 1302 is moving. In some examples, kinematic data associated with surgical instrument 1302 and maintained by computer-assisted surgical system 204 may also be used to determine the approximate direction and speed at which surgical instrument 1302 is moving. Depth data 206 may indicate a depth of both surgical instrument 1302 and structure 1308, which information may be used to determine how close surgical instrument 1302 is getting to structure 1308. System 100 may accordingly be configured to instruct computer-assisted surgical system 204 to stop the movement of surgical instrument 1302 towards structure 1308 before surgical instrument 1302 comes in contact with structure 1308.

Additionally or alternatively, system 100 may perform operation 202 by determining an amount of tissue deformation that occurs when a surgical instrument is in contact with the tissue. In this example, auxiliary sensor 214 may be implemented by a force sensor integrated into a surgical instrument controlled by computer-assisted surgical system 204. As described above, the force sensor may be configured to generate force sensing data representative of an amount of external force applied to the surgical instrument. Based on the force sensing data, system 100 may determine that the surgical instrument is in contact with tissue. In response to this determination, system 100 may use depth data 206 to determine an amount of deformation of the tissue that is caused by the surgical instrument being in contact with the tissue.

Figure 14:
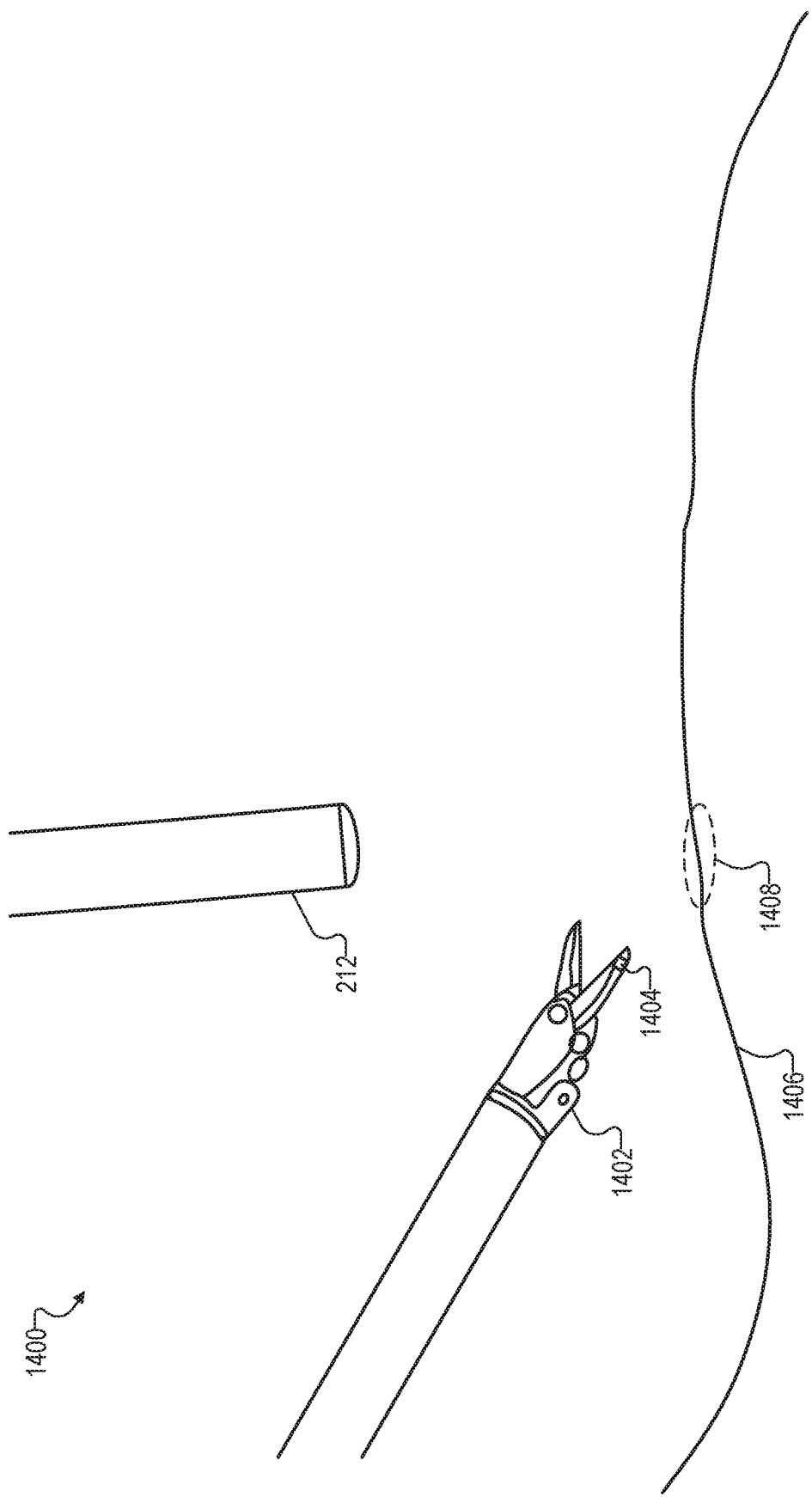
FIG. 14 shows a surgical instrument 1402 before it has come in contact with a target location according to principles described herein.
Figure 15:
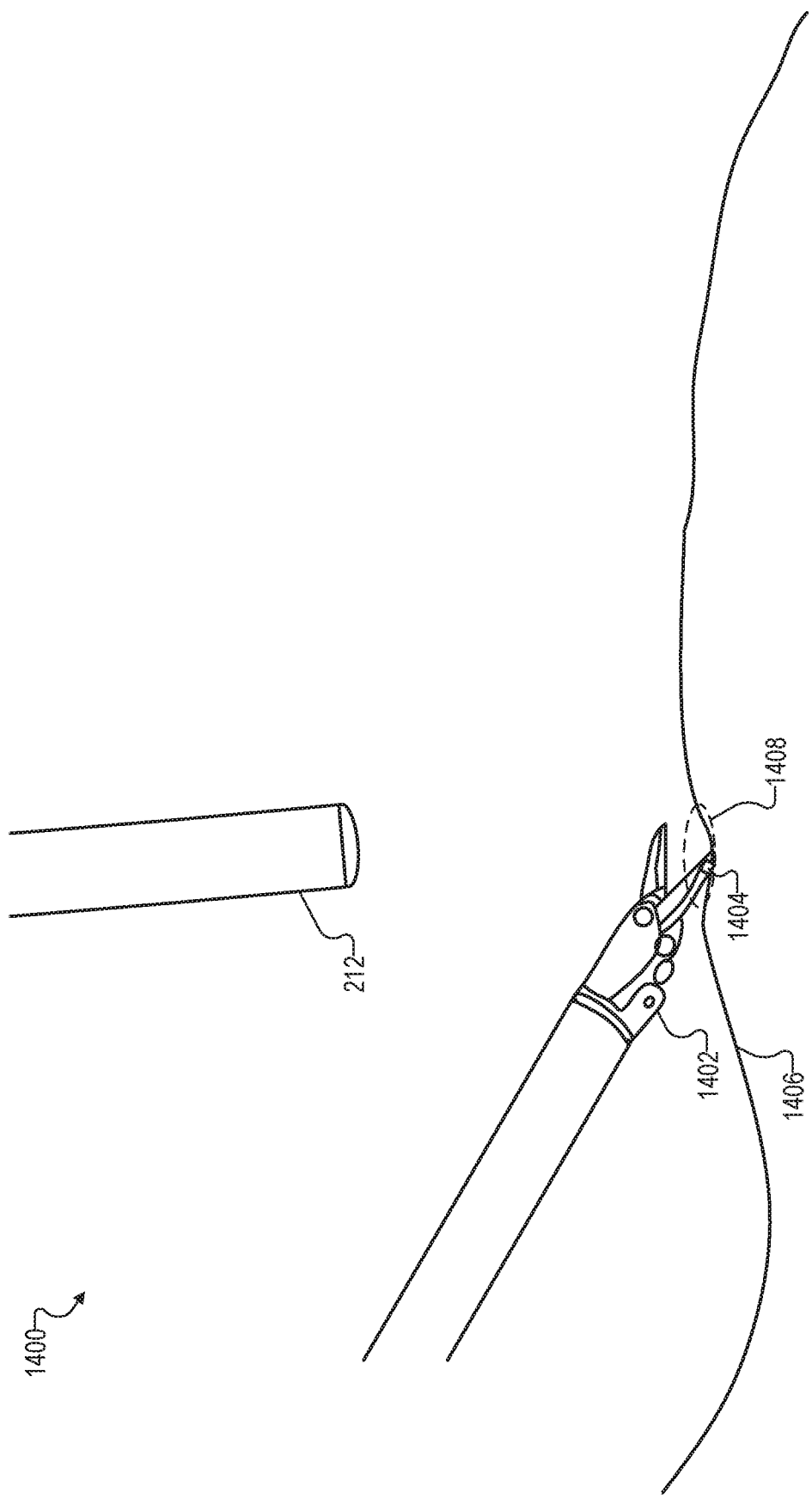
FIG. 15 shows the surgical instrument of FIG. 14 once the surgical instrument has come in contact with a target location according to principles described herein.

To illustrate, FIGS. 14-15 show an exemplary configuration 1400 in which a surgical instrument 1402 is used to perform a tissue deformation analysis operation within an internal space of a patient that is being imaged by imaging device 212. Surgical instrument 1402 may be similar to surgical instrument 1302 in that surgical instrument 1402 includes a force sensor 1404. As shown, force sensor 1404 is disposed towards a distal end of surgical instrument 1402.

In the example of FIGS. 14-15, a user may use surgical instrument 1402 to interact with tissue 1406. In particular, the user may guide surgical instrument 1402 towards a target location 1408 of tissue 1406 in order to perform the tissue deformation analysis operation with respect to target location 1408. FIG. 14 shows surgical instrument 1402 before it has come in contact with target location 1408, and FIG. 15 shows surgical instrument 1402 once it has come in contact with target location 1408.

In some examples, system 100 may obtain a first depth dataset (e.g., a first dataset included in depth data 206) while surgical instrument 1402 is not in contact with tissue 1406 (e.g., in the position shown in FIG. 14). System 100 may also obtain a second depth dataset (e.g., a second dataset included in depth data 206) while surgical instrument 1402 is in contact with target location 1408 of tissue 1406 (e.g., in the position shown in FIG. 15). Based on the first and second datasets, system 100 may determine an amount of deformation of tissue 1406 at target location 1408 that is caused by surgical instrument 1402 being in contact with target location 1408 of tissue 1406. For example, system 100 may determine a difference between the first and second depth datasets and thereby ascertain an amount of deformation of tissue 1406.

Based on the determined amount of tissue deformation, system 100 may perform one or more operations. For example, system 100 may determine a characteristic of tissue 1406 based on the amount of tissue deformation.

For example, based on the determined amount of tissue deformation, system 100 may determine a presence of a structure underneath tissue 1406. To illustrate, by measuring an amount of force applied to target location 1408 of tissue 1406 and determining a resulting amount of tissue deformation, system 100 may determine that a particular type of mass (e.g., a tumor) is underneath tissue 1406. This determination may be made in any suitable manner.

As another example, based on the determined amount of tissue deformation, system 100 may determine a difference between tissue 1408 and other tissue within the internal space of the patient. For example, if target location 1406 deforms more than a different location within tissue 1406 in response to the same amount of force, system 100 may determine that the tissue 1406 at target location 1406 is diseased, damaged, or otherwise different than the tissue 1406 at the different location.

Figure 16:
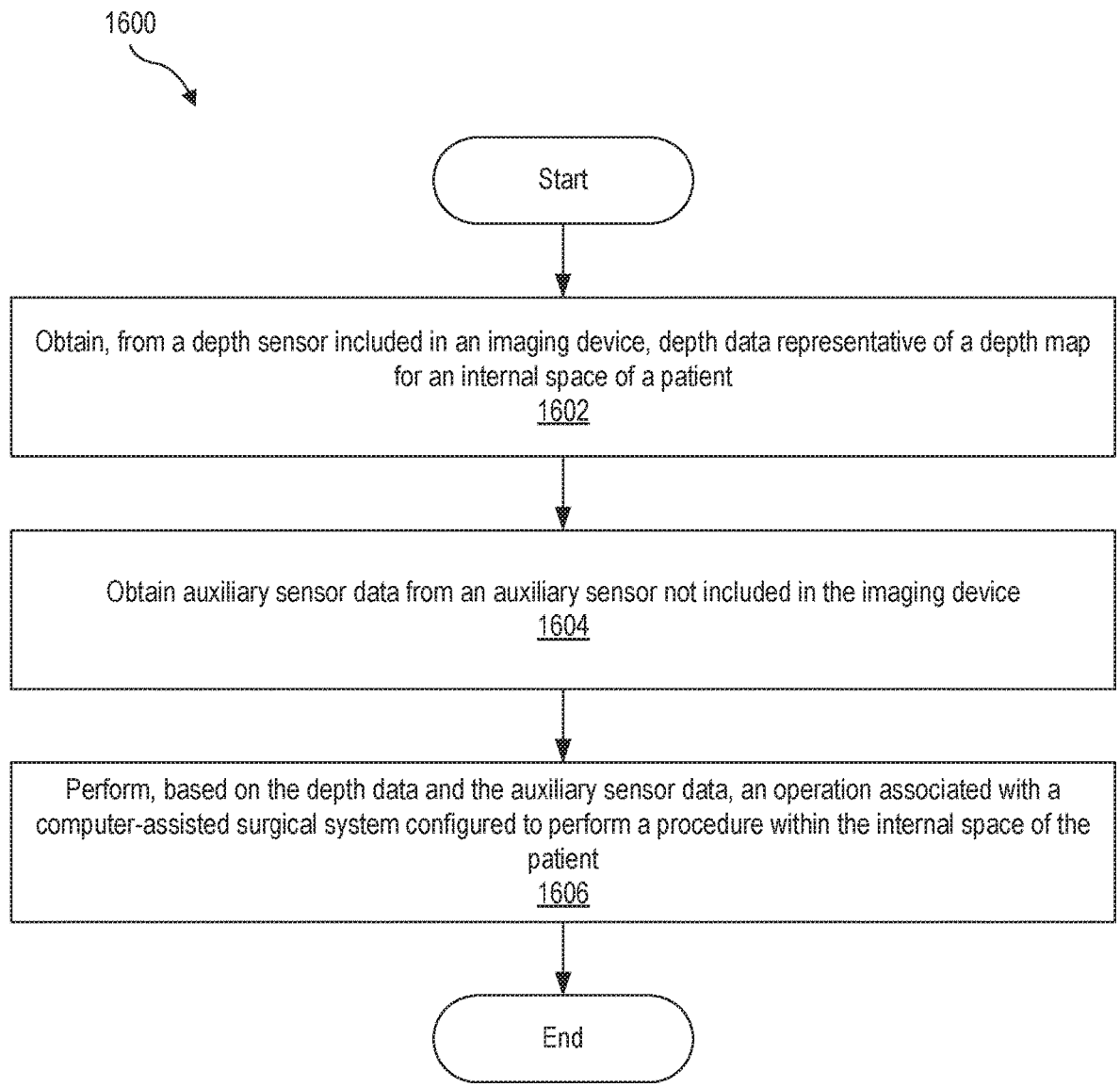
FIG. 16 illustrates an exemplary method according to principles described herein.

FIG. 16 illustrates an exemplary method 1600 that may be performed by an operation management system (e.g., system 100 and/or any implementation thereof). While FIG. 16 illustrates exemplary operations according to one embodiment, other embodiments may omit, add to, reorder, and/or modify any of the operations shown in FIG. 16.

In operation 1602, an operation management system obtains, from a depth sensor included in an imaging device, depth data representative of a depth map for an internal space of a patient. Operation 1602 may be performed in any of the ways described herein.

In operation 1604, the operation management system obtains auxiliary sensor data from an auxiliary sensor not included in the imaging device. Operation 1604 may be performed in any of the ways described herein.

In operation 1606, the operation management system performs, based on the depth data and the auxiliary sensor data, an operation associated with a computer-assisted surgical system configured to perform a procedure within the internal space of the patient. Operation 1606 may be performed in any of the ways described herein.

Figure 17:
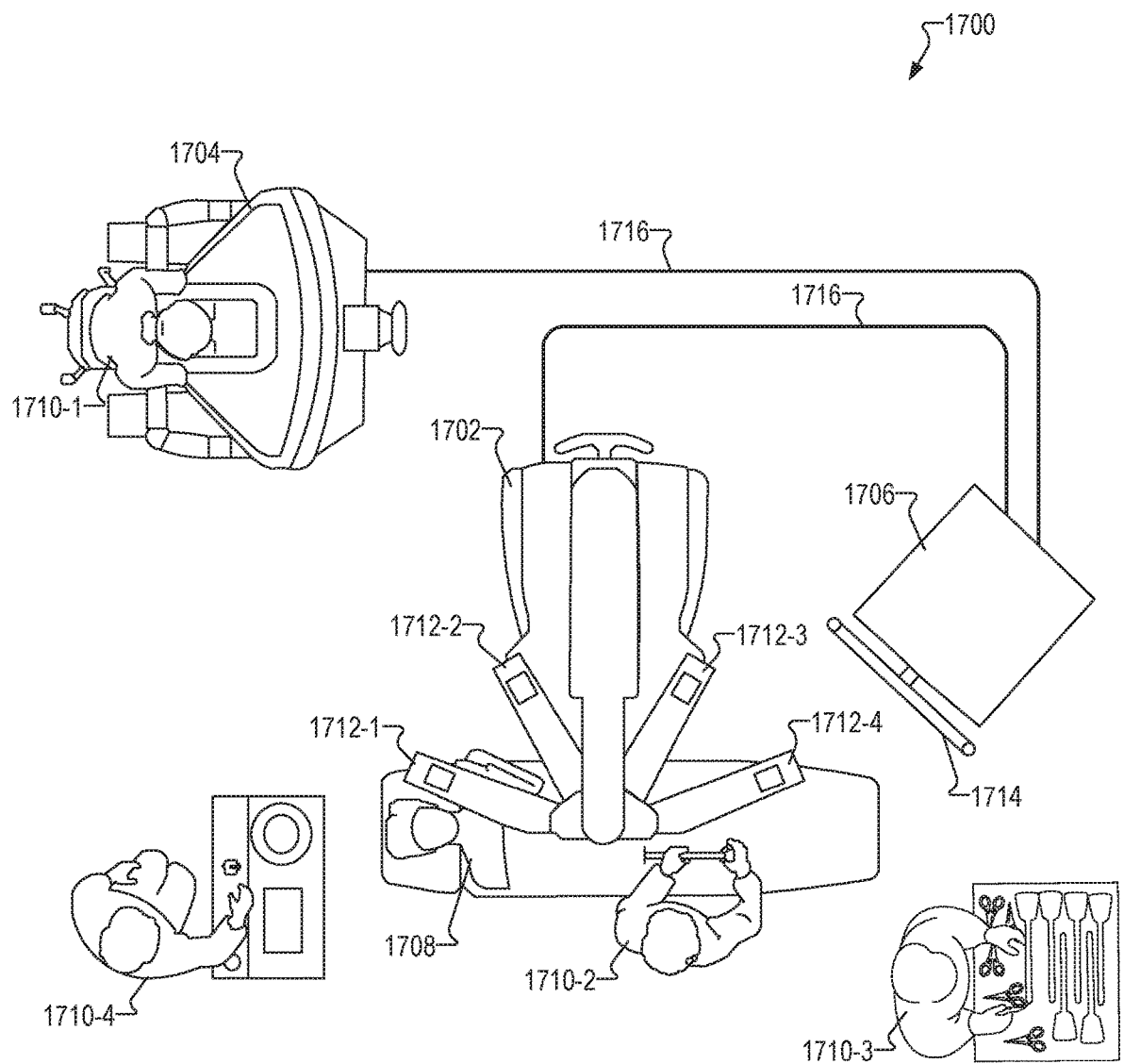
FIG. 17 illustrates an exemplary computer-assisted surgical system according to principles described herein.

FIG. 17 illustrates an exemplary computer-assisted surgical system 1700 ("surgical system 1700"). Surgical system 1700 may be an implementation of computer-assisted surgical system 204. As shown, surgical system 1700 may include a manipulating system 1702, a user control system 1704, and an auxiliary system 1706 communicatively coupled one to another. Surgical system 1700 may be utilized by a surgical team to perform a computer-assisted surgical procedure on a patient 1708. As shown, the surgical team may include a surgeon 1710-1, an assistant 1710-2, a nurse 1710-3, and an anesthesiologist 1710-4, all of whom may be collectively referred to as "surgical team members 1710." Additional or alternative surgical team members may be present during a surgical session as may serve a particular implementation.

While FIG. 17 illustrates an ongoing minimally invasive surgical procedure, it will be understood that surgical system 1700 may similarly be used to perform open surgical procedures or other types of surgical procedures that may similarly benefit from the accuracy and convenience of surgical system 1700. Additionally, it will be understood that the surgical session throughout which surgical system 1700 may be employed may not only include an operative phase of a surgical procedure, as is illustrated in FIG. 17, but may also include preoperative, postoperative, and/or other suitable phases of the surgical procedure. A surgical procedure may include any procedure in which manual and/or instrumental techniques are used on a patient to investigate or treat a physical condition of the patient.

As shown in FIG. 17, manipulating system 1702 may include a plurality of manipulator arms 1712 (e.g., manipulator arms 1712-1 through 1712-4) to which a plurality of surgical instruments may be coupled. Each surgical instrument may be implemented by any suitable surgical tool (e.g., a tool having tissue-interaction functions), medical tool, imaging device (e.g., an endoscope), sensing instrument (e.g., a force-sensing surgical instrument), diagnostic instrument, or the like that may be used for a computer-assisted surgical procedure on patient 1708 (e.g., by being at least partially inserted into patient 1708 and manipulated to perform a computer-assisted surgical procedure on patient 1708). While manipulating system 1702 is depicted and described herein as including four manipulator arms 1712, it will be recognized that manipulating system 1702 may include only a single manipulator arm 1712 or any other number of manipulator arms as may serve a particular implementation.

Manipulator arms 1712 and/or surgical instruments attached to manipulator arms 1712 may include one or more displacement transducers, orientational sensors, and/or positional sensors used to generate raw (i.e., uncorrected) kinematics information. One or more components of surgical system 1700 may be configured to use the kinematics information to track (e.g., determine positions of) and/or control the surgical instruments.

User control system 1704 may be configured to facilitate control by surgeon 1710-1 of manipulator arms 1712 and surgical instruments attached to manipulator arms 1712. For example, surgeon 1710-1 may interact with user control system 1704 to remotely move or manipulate manipulator arms 1712 and the surgical instruments. To this end, user control system 1704 may provide surgeon 1710-1 with imagery (e.g., high-definition 3D imagery) of a surgical area associated with patient 1708 as captured by an imaging system (e.g., any of the medical imaging systems described herein). In certain examples, user control system 1704 may include a stereo viewer having two displays where stereoscopic images of a surgical area associated with patient 1708 and generated by a stereoscopic imaging system may be viewed by surgeon 1710-1. Surgeon 1710-1 may utilize the imagery to perform one or more procedures with one or more surgical instruments attached to manipulator arms 1712.

To facilitate control of surgical instruments, user control system 1704 may include a set of master controls. These master controls may be manipulated by surgeon 1710-1 to control movement of surgical instruments (e.g., by utilizing robotic and/or teleoperation technology). The master controls may be configured to detect a wide variety of hand, wrist, and finger movements by surgeon 1710-1. In this manner, surgeon 1710-1 may intuitively perform a procedure using one or more surgical instruments.

Auxiliary system 1706 may include one or more computing devices configured to perform primary processing operations of surgical system 1700. In such configurations, the one or more computing devices included in auxiliary system 1706 may control and/or coordinate operations performed by various other components (e.g., manipulating system 1702 and user control system 1704) of surgical system 1700. For example, a computing device included in user control system 1704 may transmit instructions to manipulating system 1702 by way of the one or more computing devices included in auxiliary system 1706. As another example, auxiliary system 1706 may receive, from manipulating system 1702, and process image data representative of imagery captured by an imaging device attached to one of manipulator arms 1712.

In some examples, auxiliary system 1706 may be configured to present visual content to surgical team members 1710 who may not have access to the images provided to surgeon 1710-1 at user control system 1704. To this end, auxiliary system 1706 may include a display monitor 1714 configured to display one or more user interfaces, such as images (e.g., 2D images) of the surgical area, information associated with patient 1708 and/or the surgical procedure, and/or any other visual content as may serve a particular implementation. For example, display monitor 1714 may display images of the surgical area together with additional content (e.g., graphical content, contextual information, etc.)

concurrently displayed with the images. In some embodiments, display monitor 1714 is implemented by a touchscreen display with which surgical team members 1710 may interact (e.g., by way of touch gestures) to provide user input to surgical system 1700.

Manipulating system 1702, user control system 1704, and auxiliary system 1706 may be communicatively coupled one to another in any suitable manner. For example, as shown in FIG. 17, manipulating system 1702, user control system 1704, and auxiliary system 1706 may be communicatively coupled by way of control lines 1716, which may represent any wired or wireless communication link as may serve a particular implementation. To this end, manipulating system 1702, user control system 1704, and auxiliary system 1706 may each include one or more wired or wireless communication interfaces, such as one or more local area network interfaces, Wi-Fi network interfaces, cellular interfaces, etc.

In some examples, a non-transitory computer-readable medium storing computer-readable instructions may be provided in accordance with the principles described herein. The instructions, when executed by a processor of a computing device, may direct the processor and/or computing device to perform one or more operations, including one or more of the operations described herein. Such instructions may be stored and/or transmitted using any of a variety of known computer-readable media.

A non-transitory computer-readable medium as referred to herein may include any non-transitory storage medium that participates in providing data (e.g., instructions) that may be read and/or executed by a computing device (e.g., by a processor of a computing device). For example, a non-transitory computer-readable medium may include, but is not limited to, any combination of non-volatile storage media and/or volatile storage media. Exemplary non-volatile storage media include, but are not limited to, read-only memory, flash memory, a solid-state drive, a magnetic storage device (e.g. a hard disk, a floppy disk, magnetic tape, etc.), ferroelectric random-access memory ("RAM"), and an optical disc (e.g., a compact disc, a digital video disc, a Blu-ray disc, etc.). Exemplary volatile storage media include, but are not limited to, RAM (e.g., dynamic RAM).

Figure 18:
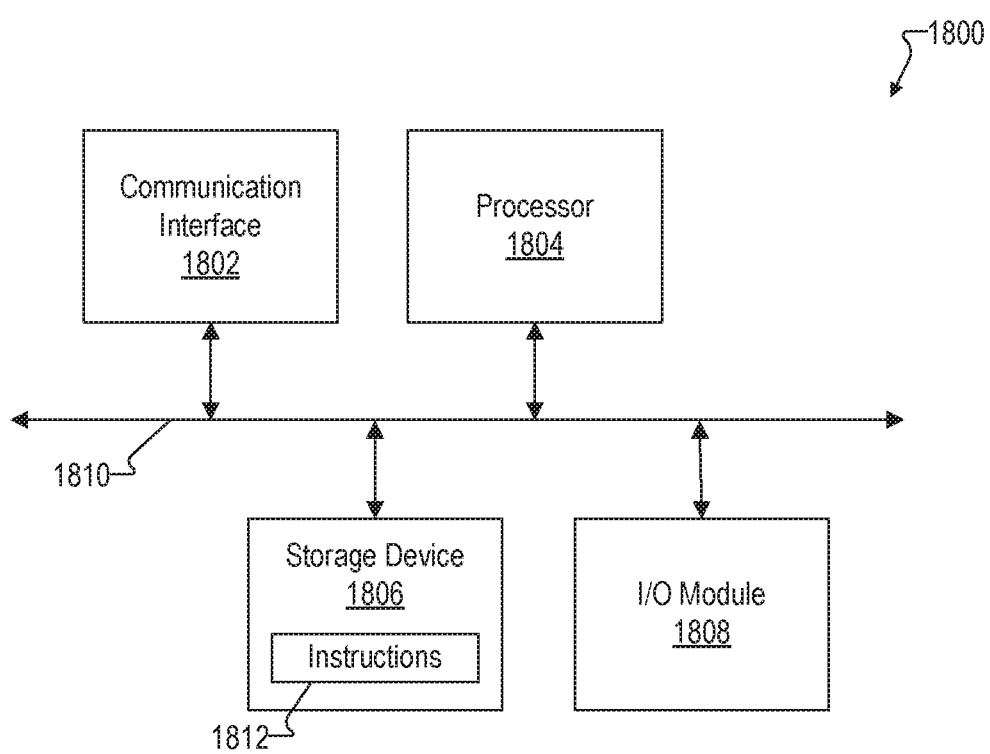
FIG. 18 illustrates an exemplary computing device according to principles described herein.

FIG. 18 illustrates an exemplary computing device 1800 that may be specifically configured to perform one or more of the processes described herein. Any of the systems, computing devices, and/or other components described herein may be implemented by computing device 1800.

As shown in FIG. 18, computing device 1800 may include a communication interface 1802, a processor 1804, a storage device 1806, and an input/output (I/O") module 1808 communicatively connected one to another via a communication infrastructure 1810, While an exemplary computing device 1800 is shown in FIG. 18, the components illustrated in FIG. 18 are not intended to be limiting. Additional or alternative components may be used in other embodiments. Components of computing device 1800 shown in FIG. 18 will now be described in additional detail.

Communication interface 1802 may be configured to communicate with one or more computing devices. Examples of communication interface 1802 include, without limitation, a wired network interface (such as a network interface card), a wireless network interface (such as a wireless network interface card), a modem, an audio/video connection, and any other suitable interface.

Processor 1804 generally represents any type or form of processing unit capable of processing data and/or interpreting, executing, and/or directing execution of one or more of the instructions, processes, and/or operations described herein. Processor 1804 may perform operations by executing computer-executable instructions 1812 (e.g., an application, software, code, and/or other executable data instance) stored in storage device 1806.

Storage device 1806 may include one or more data storage media, devices, or configurations and may employ any type, form, and combination of data storage media and/or device. For example, storage device 1806 may include, but is not limited to, any combination of the non-volatile media and/or volatile media described herein, Electronic data, including data described herein, may be temporarily and/or permanently stored in storage device 1806. For example, data representative of computer-executable instructions 1812 configured to direct processor 1804 to perform any of the operations described herein may be stored within storage device 1806. In some examples, data may be arranged in one or more databases residing within storage device 1806.

I/O module 1808 may include one or more I/O modules configured to receive user input and provide user output. I/O module 1808 may include any hardware, firmware, software, or combination thereof supportive of input and output capabilities. For example, I/O module 1808 may include hardware and/or software for capturing user input, including, but not limited to, a keyboard or keypad, a touchscreen component (e.g., touchscreen display), a receiver (e.g., an RF or infrared receiver), motion sensors, and/or one or more input buttons.

I/O module 1808 may include one or more devices for presenting output to a user, including, but not limited to, a graphics engine, a display (e.g., a display screen), one or more output drivers (e.g., display drivers), one or more audio speakers, and one or more audio drivers. In certain embodiments, I/O module 1808 is configured to provide graphical data to a display for presentation to a user. The graphical data may be representative of one or more graphical user interfaces and/or any other graphical content as may serve a particular implementation.

In the preceding description, various exemplary embodiments have been described with reference to the accompanying drawings. It will, however, be evident that various modifications and changes may be made thereto, and additional embodiments may be implemented, without departing from the scope of the invention as set forth in the claims that follow. For example, certain features of one embodiment described herein may be combined with or substituted for features of another embodiment described herein. The description and drawings are accordingly to be regarded in an illustrative rather than a restrictive sense.

What is claimed is:
1. A system, comprising:
a memory storing instructions; and
a processor communicatively coupled to the memory and configured to execute the instructions to:
obtain, from a depth sensor included in an imaging device, depth data representative of a depth map for an internal space of a patient;
obtain, from a force sensor integrated into a surgical instrument controlled by a computer-assisted surgical system, force sensing data representative of an amount of external force applied to the surgical instrument; and
perform, based on the depth data and the force sensing data, an operation associated with the computer-assisted surgical system configured to perform a procedure within the internal space of the patient.

2. The system of claim 1, wherein:
the depth sensor comprises a time-of-flight sensor in the imaging device; and
the obtaining of the depth data representative of the depth map comprises:
directing the time-of-flight sensor to acquire the depth data; and
receiving the depth data from the time-of-flight sensor.

3. The system of claim 2, wherein the imaging device further comprises a visible light camera configured to acquire a two-dimensional visible light image of the internal space.

4. The system of claim 2, wherein:
the processor is further configured to execute the instructions to receive user input data indicating a selection by a user of a first two-dimensional endpoint within an image of the internal space, the first two-dimensional endpoint corresponding to a first feature within the internal space as depicted by the image; and
the performing of the operation associated with the computer-assisted surgical system further comprises:
defining, based on the depth data and on the user input data, a first three-dimensional endpoint corresponding to the first feature; and
determining, based on the depth data, a distance from the first three-dimensional endpoint corresponding to the first feature to a second three-dimensional endpoint corresponding to a second feature within the internal space.

5. The system of claim 4, wherein:
the processor is further configured to execute the instructions to receive additional user input data indicating a selection of a second two-dimensional endpoint within the image, the second two-dimensional endpoint corresponding to the second feature; and
the performing of the operation associated with the computer-assisted surgical system further comprises defining, based on the depth data and the additional user input data, the second three-dimensional endpoint corresponding to the second feature.

6. The system of claim 1, wherein:
the depth sensor comprises a first visible light camera in the imaging device and a second visible light camera in the imaging device; and
the obtaining of the depth data representative of the depth map comprises:
directing the first visible light camera to acquire a first image of the internal space,
directing the second visible light camera to acquire a second image of the internal space, and
generating, based on the first and second images, the depth map.

7. The system of claim 1, wherein:
the performing of the operation associated with the computer-assisted surgical system comprises:
determining, based on the depth data and on the force sensing data, that the surgical instrument begins moving towards a structure located in the internal space in response to the external force applied to the surgical instrument; and
instructing, in response to the determining that the surgical instrument begins moving towards the structure, the computer-assisted surgical system to stop the movement of the surgical instrument towards the structure.

8. The system of claim 1, wherein:
the obtaining of the depth data comprises obtaining a first depth dataset while a surgical instrument controlled by the computer-assisted surgical system is not in contact with tissue in the internal space of the patient and a second depth dataset while the surgical instrument is in contact with the tissue; and
the performing of the operation associated with the computer-assisted surgical system comprises:
determining, based on the force sensing data, that the surgical instrument is in contact with the tissue, and
determining, in response to the determining that the surgical instrument is in contact with the tissue and based on the first and second depth datasets, an amount of deformation of the tissue that is caused by the surgical instrument being in contact with the tissue.

9. The system of claim 8, wherein the processor is further configured to execute the instructions to determine a characteristic of the tissue based on the amount of deformation.

10. The system of claim 1, wherein the force is applied to the surgical instrument by an object not being controlled by the computer-assisted surgical system.

11. A method comprising:
obtaining, by an operation management system from a depth sensor included in an imaging device, depth data representative of a depth map for an internal space of a patient;
obtaining, by the operation management system from a force sensor integrated into a surgical instrument controlled by a computer-assisted surgical system, force sensing data representative of an amount of external force applied to the surgical instrument, auxiliary sensor data from an auxiliary sensor not included in the imaging device; and
performing, by the operation management system based on the depth data and the force sensing data, an operation associated with the computer-assisted surgical system configured to perform a procedure within the internal space of the patient.

12. The method of claim 11, wherein:
the depth sensor comprises a time-of-flight sensor in the imaging device; and
the obtaining of the depth data representative of the depth map comprises:
directing the time-of-flight sensor to acquire the depth data; and
receiving the depth data from the time-of-flight sensor.

13. The method of claim 12, wherein the imaging device further comprises a visible light camera configured to acquire a two-dimensional visible light image of the internal space.

14. The method of claim 12, wherein:
the method further comprises receiving user input data indicating a selection by a user of a first two-dimensional endpoint within an image of the internal space, the first two-dimensional endpoint corresponding to a first feature within the internal space as depicted by the image; and
the performing of the operation associated with the computer-assisted surgical system further comprises:
defining, based on the depth data and on the user input data, a first three-dimensional endpoint corresponding to the first feature; and
determining, based on the depth data, a distance from the first three-dimensional endpoint corresponding to the first feature to a second three-dimensional endpoint corresponding to a second feature within the internal space.

15. The method of claim 14, wherein:

further comprising receiving additional user input data indicating a selection of a second two-dimensional endpoint within the image, the second two-dimensional endpoint corresponding to the second feature; and the performing of the operation associated with the computer-assisted surgical system further comprises defining, based on the depth data and the additional user input data, the second three-dimensional endpoint corresponding to the second feature.

16. The method of claim 11, wherein:

the depth sensor comprises a first visible light camera in the imaging device and a second visible light camera in the imaging device; and the obtaining of the depth data representative of the depth map comprises:

directing the first visible light camera to acquire a first image of the internal space, directing the second visible light camera to acquire a second image of the internal space, and generating, based on the first and second images, the depth map.

17. The method of claim 11, wherein:

the performing of the operation associated with the computer-assisted surgical system comprises:

determining, based on the depth data and on the force sensing data, that the surgical instrument begins moving towards a structure located in the internal space in response to the external force applied to the surgical instrument; and instructing, in response to the determining that the surgical instrument begins moving towards the structure, the computer-assisted surgical system to stop the movement of the surgical instrument towards the structure.

18. The method of claim 11, wherein:

the obtaining of the depth data comprises obtaining a first depth dataset while a surgical instrument controlled by the computer-assisted surgical system is not in contact with tissue in the internal space of the patient and a second depth dataset while the surgical instrument is in contact with the tissue; and the performing of the operation associated with the computer-assisted surgical system comprises:

determining, based on the force sensing data, that the surgical instrument is in contact with the tissue, and determining, in response to the determining that the surgical instrument is in contact with the tissue and based on the first and second depth datasets, an amount of deformation of the tissue that is caused by the surgical instrument being in contact with the tissue.

19. The method of claim 18, further comprising determining, by the operation management system, a characteristic of the tissue based on the amount of deformation.

20. A non-transitory computer-readable medium storing instructions that, when executed, direct a processor of a computing device to:

obtain, from a depth sensor included in an imaging device, depth data representative of a depth map for an internal space of a patient;

obtain, from a force sensor integrated into a surgical instrument controlled by a computer-assisted surgical system, force sensing data representative of an amount of external force applied to the surgical instrument; and perform, based on the depth data and the force sensing data, an operation associated with the computer-assisted surgical system configured to perform a procedure within the internal space of the patient.

* * * * *